United States Patent
Darabian

(10) Patent No.: US 12,245,762 B2
(45) Date of Patent: Mar. 11, 2025

(54) TRANSCATHETER HEART VALVE LEAFLET PLICATION

(71) Applicant: EDWARDS LIFESCIENCES CORPORATION, Irvine, CA (US)

(72) Inventor: Sirous Darabian, Lake Forest, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/510,520

(22) Filed: Nov. 15, 2023

(65) Prior Publication Data
US 2024/0081811 A1 Mar. 14, 2024

Related U.S. Application Data

(60) Continuation of application No. 16/864,474, filed on May 1, 2020, now Pat. No. 11,849,937, which is a
(Continued)

(51) Int. Cl.
*A61B 17/04* (2006.01)
*A61B 17/00* (2006.01)
*A61B 17/06* (2006.01)

(52) U.S. Cl.
CPC ...... *A61B 17/0482* (2013.01); *A61B 17/0401* (2013.01); *A61B 17/0469* (2013.01);
(Continued)

(58) Field of Classification Search
CPC ............ A61B 17/0482; A61B 17/0401; A61B 17/0469; A61B 17/06066; A61B 17/0487;
(Continued)

(56) References Cited

U.S. PATENT DOCUMENTS 6,626,930 B1 9/2003 Allen et al.
7,011,669 B2 3/2006 Kimblad
(Continued)

FOREIGN PATENT DOCUMENTS

WO 0234167 A2 5/2002
WO 2007098212 A2 8/2007
(Continued)

OTHER PUBLICATIONS

Devereux RB, Kramer-Fox R, Kligfield P. Mitral valve prolapse: causes, clinical manifestations, and management. Ann Intern Med. 1989;111: 305-317.
(Continued)

*Primary Examiner* — Sarah W Aleman
*Assistant Examiner* — Mikail A Mannan
(74) *Attorney, Agent, or Firm* — Edwards Lifesciences

(57) ABSTRACT

Apparatus for repairing a leaflet of a heart valve can include a leaflet-plicating tool that can include leaflet-capture arms and a helical needle. The needle can be operatively coupled to the leaflet-capture arms. The leaflet-capture arms can include an arm-shaft, each configured to house a leaflet-engaging member. The leaflet-capture arms can be configured to use the leaflet-engaging members, extended over the leaflet from the annulus toward a free edge of the leaflet, to form a plication in the leaflet of the heart valve between the leaflet-capture arms. The leaflet-plicating tool can be configured to secure the plication by using the helical needle to stitch a suture helically along the plication. Other embodiments are also described.

26 Claims, 13 Drawing Sheets

Related U.S. Application Data division of application No. 15/843,261, filed on Dec. 15, 2017, now Pat. No. 10,675,017.

(60) Provisional application No. 62/455,831, filed on Feb. 7, 2017.

(52) U.S. Cl.
CPC .................. *A61B 17/06066* (2013.01); *A61B 2017/00243* (2013.01); *A61B 2017/00292* (2013.01); *A61B 2017/00367* (2013.01); *A61B 2017/00783* (2013.01); *A61B 2017/0409* (2013.01); *A61B 2017/0464* (2013.01); *A61B 17/0487* (2013.01); *A61B 2017/0488* (2013.01); *A61B 2017/06076* (2013.01)

(58) Field of Classification Search
CPC .......... A61B 17/0485; A61B 17/06166; A61B 2017/00243; A61B 2017/0464; A61B 2017/00867; A61B 2017/06076; A61B 2017/00783; A61F 2/2457; A61F 2/0811; A61F 2220/0075
See application file for complete search history.

(56) References Cited

U.S. PATENT DOCUMENTS

| | | | |
|---|---|---|---|
| 7,025,791 B2 | 4/2006 | Levine et al. | |
| 7,527,646 B2 | 5/2009 | Rahdert et al. | |
| 7,618,449 B2 | 11/2009 | Tremulis et al. | |
| 7,628,797 B2 | 12/2009 | Tieu et al. | |
| 8,366,767 B2 | 2/2013 | Zhang | |
| 8,398,708 B2 | 3/2013 | Meiri et al. | |
| 8,403,983 B2 | 3/2013 | Quadri et al. | |
| 8,579,964 B2 | 11/2013 | Lane et al. | |
| 8,778,017 B2 | 7/2014 | Eliasen et al. | |
| 8,926,690 B2 | 1/2015 | Kovalsky | |
| 8,956,404 B2 | 2/2015 | Bortlein et al. | |
| 2004/0127982 A1 | 7/2004 | Machold et al. | |
| 2005/0159810 A1 | 7/2005 | Filsoufi | |
| 2005/0177180 A1 | 8/2005 | Kaganov et al. | |
| 2006/0030885 A1 | 2/2006 | Hyde | |
| 2006/0173524 A1 | 8/2006 | Salahieh et al. | |
| 2006/0241745 A1 | 10/2006 | Solem | |
| 2006/0264980 A1 | 11/2006 | Khairkhahan et al. | |
| 2007/0038293 A1* | 2/2007 | St. Goar ......... A61B 17/00234 | |
| | | | 623/2.11 |
| 2007/0049942 A1 | 3/2007 | Hindrichs et al. | |
| 2007/0093890 A1 | 4/2007 | Eliasen et al. | |
| 2007/0219612 A1 | 9/2007 | Andreas et al. | |
| 2007/0244554 A1 | 10/2007 | Rafiee et al. | |
| 2007/0244555 A1 | 10/2007 | Rafiee et al. | |
| 2007/0244556 A1 | 10/2007 | Rafiee et al. | |
| 2007/0282375 A1 | 12/2007 | Hindrichs et al. | |
| 2007/0282429 A1 | 12/2007 | Hauser et al. | |
| 2008/0065011 A1 | 3/2008 | Marchand et al. | |
| 2008/0281356 A1 | 11/2008 | Chau et al. | |
| 2008/0288061 A1 | 11/2008 | Maurer et al. | |
| 2009/0043381 A1 | 2/2009 | Macoviak et al. | |
| 2009/0048668 A1 | 2/2009 | Wilson et al. | |
| 2009/0105816 A1 | 4/2009 | Olsen et al. | |
| 2009/0171456 A1 | 7/2009 | Kveen et al. | |
| 2009/0281619 A1 | 11/2009 | Le et al. | |
| 2010/0010538 A1 | 1/2010 | Juravic et al. | |
| 2011/0106247 A1 | 5/2011 | Miller et al. | |
| 2011/0137397 A1 | 6/2011 | Chau et al. | |
| 2011/0184510 A1 | 7/2011 | Maisano et al. | |
| 2011/0208290 A1 | 8/2011 | Straubinger et al. | |
| 2011/0282361 A1 | 11/2011 | Miller et al. | |
| 2012/0022633 A1 | 1/2012 | Olson et al. | |
| 2012/0078350 A1 | 3/2012 | Wang et al. | |
| 2012/0143226 A1 | 6/2012 | Belson et al. | |
| 2012/0197388 A1 | 8/2012 | Khairkhahan et al. |
| 2012/0203336 A1 | 8/2012 | Annest |
| 2012/0245604 A1 | 9/2012 | Tegzes |
| 2012/0253386 A1 | 10/2012 | Rowe et al. |
| 2013/0138121 A1 | 5/2013 | Allen et al. |
| 2014/0031864 A1 | 1/2014 | Jafari et al. |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0114404 A1 | 4/2014 | Gammie et al. |
| 2014/0148828 A1 | 5/2014 | Ewers et al. |
| 2014/0222137 A1 | 8/2014 | Miller et al. |
| 2014/0277426 A1 | 9/2014 | Dakin et al. |
| 2015/0119981 A1 | 4/2015 | Khairkhahan et al. |
| 2015/0230919 A1 | 8/2015 | Chau et al. |
| 2015/0297212 A1 | 10/2015 | Reich et al. |
| 2015/0366556 A1 | 12/2015 | Khairkhahan et al. |
| 2016/0015512 A1 | 1/2016 | Zhang et al. |
| 2016/0287383 A1 | 10/2016 | Rowe |
| 2016/0302917 A1 | 10/2016 | Schewel |
| 2017/0086975 A1 | 3/2017 | Gilmore et al. |
| 2017/0095332 A1 | 4/2017 | Bruchman |
| 2017/0100119 A1 | 4/2017 | Baird et al. |
| 2017/0189186 A1 | 7/2017 | Mohl |
| 2017/0245993 A1 | 8/2017 | Gross et al. |
| 2018/0221014 A1 | 8/2018 | Darabian |
| 2018/0325663 A1 | 11/2018 | Taylor et al. |
| 2019/0076249 A1 | 3/2019 | Khairkhahan et al. |
| 2019/0117113 A1 | 4/2019 | Curran |
| 2019/0175344 A1 | 6/2019 | Khairkhahan |
| 2019/0192296 A1 | 6/2019 | Schwartz et al. |
| 2019/0201191 A1 | 7/2019 | McLean et al. |
| 2019/0290431 A1 | 9/2019 | Genovese et al. |
| 2019/0290432 A1 | 9/2019 | Duffy et al. |
| 2019/0350705 A1 | 11/2019 | Schewel et al. |
| 2020/0268512 A1 | 8/2020 | Mohl |
| 2021/0338418 A1 | 11/2021 | Feld |
| 2022/0133327 A1 | 5/2022 | Zhang et al. |
| 2022/0257196 A1 | 8/2022 | Massmann |
| 2023/0014540 A1 | 1/2023 | Metchik et al. |

FOREIGN PATENT DOCUMENTS

| | | |
|---|---|---|
| WO | 2014162343 A1 | 10/2014 |
| WO | 2019116322 A1 | 6/2019 |
| WO | 2022157592 A1 | 7/2022 |
| WO | 2022250983 A1 | 12/2022 |
| WO | 2023003755 A1 | 1/2023 |
| WO | 2023004098 A1 | 1/2023 |
| WO | 2023288003 A1 | 1/2023 |

OTHER PUBLICATIONS

Jones EC, Devereux RB, Roman MJ, et al. Prevalence and correlates of mitral regurgitation in a population-based sample (the Strong Heart Study). Am J Cardiol 2001; 87:298.

Levy D, Savage D. Prevalence and clinical features of mitral valve prolapse. Am Heart J 1987;113:1281-1290.

McGoon D. Repair of mitral valve insufficiency due to ruptured chordae tendiae. J Thorac Cardiovasc Surg 1960;39:357-62.

Nkomo VT, Gardin JM, Skelton TN, Gottdiener JS, Scott CG, Enriquez Sarano M, et al. Burden of valvular heart diseases: a population-based study. Lancet. 2006;368:1005-11.

Perier P, Stumpf J, Götz C, et al. Valve repair for mitral regurgitation caused by isolated prolapse of the posterior leaflet. Ann Thorac Surg 1997;64:445-50.

Warth DC, King ME, Cohen JM, Tesoriero VL, Marcus E, Weyman AE. Prevalence of mitral valve prolapse in normal children. J Am Coll Cardiol 1985;5:1173-1177.

Wilcken DEL, Hickey AJ. Lifetime risk for patients with mitral valve prolapse of developing severe valve regurgitation requiring surgery. Circulation 1988;78:10-14.

\* cited by examiner

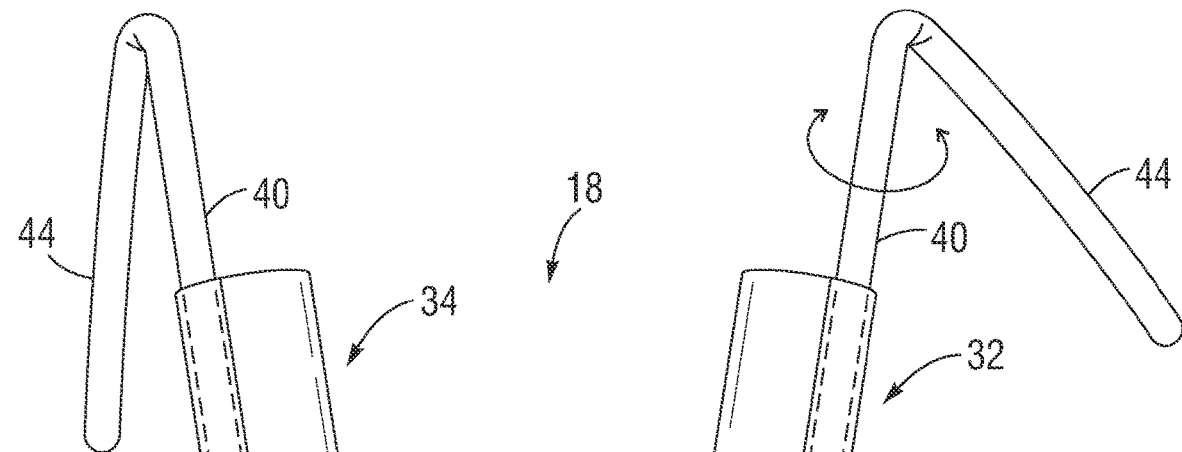
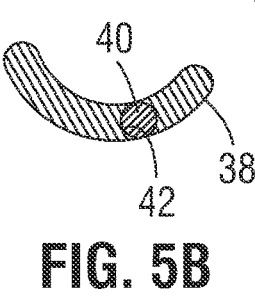
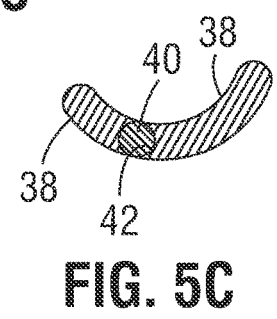
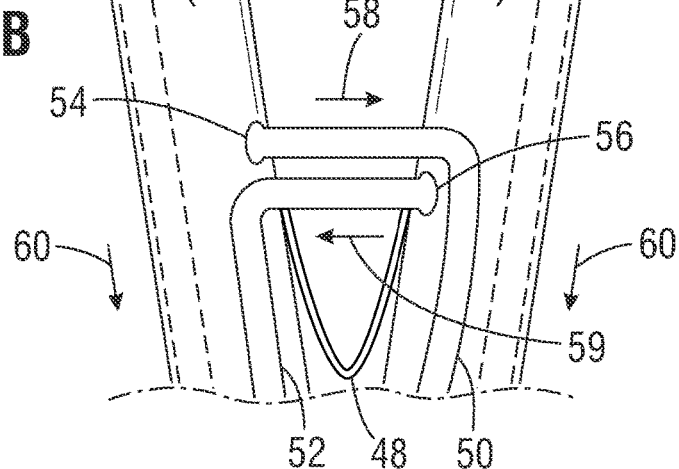
FIG. 5A
FIG. 5B
FIG. 5C

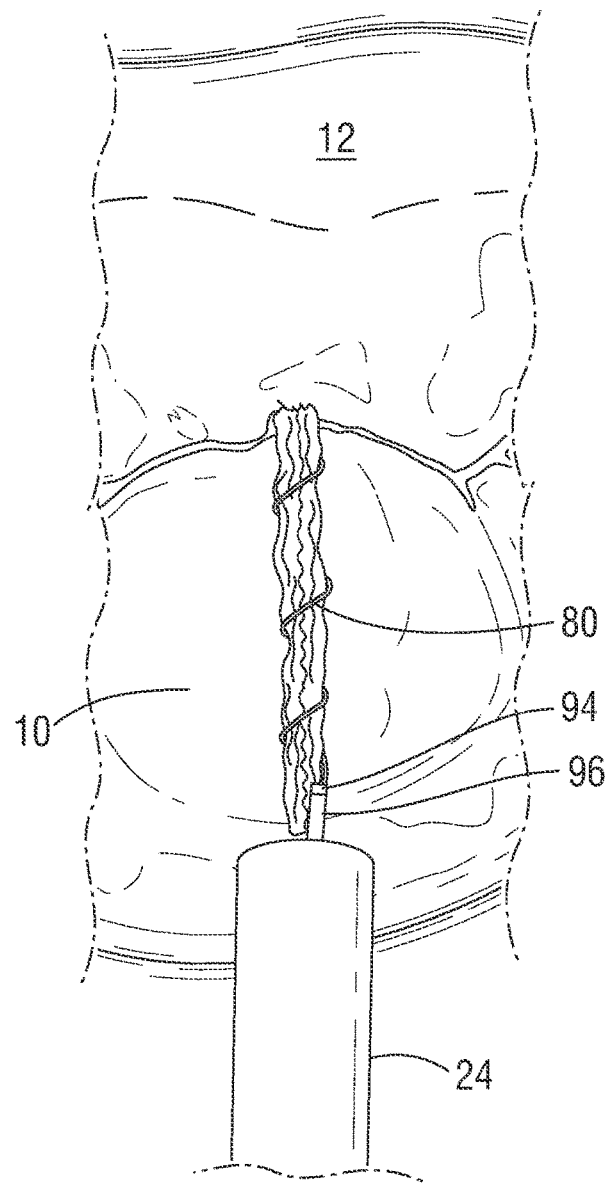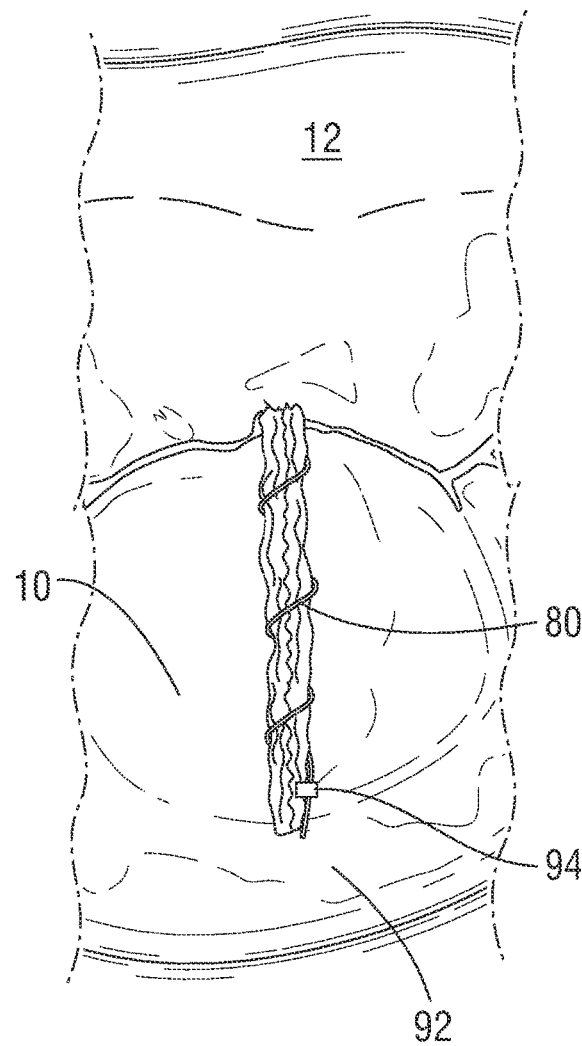

TRANSCATHETER HEART VALVE LEAFLET PLICATION

CROSS-REFERENCE TO RELATED APPLICATION

The present application is a Continuation of U.S. patent application Ser. No. 16/864,474 to Darabian, filed May 1, 2020; which is a Divisional of U.S. patent application Ser. No. 15/843,261 to Darabian, filed Dec. 15, 2017 (now U.S. Pat. No. 10,675,017); which claims the benefit of U.S. Provisional Application No. 62/455,831, filed Feb. 7, 2017. All of the above-cited documents are incorporated herein by reference in their entireties.

FIELD

The present disclosure generally relates to heart valve repair, and more particularly to devices and related methods for improving coaptation between heart valve leaflets.

BACKGROUND

The native heart valves (i.e., the aortic, pulmonary, tricuspid, and mitral valves) serve critical functions in assuring the unidirectional flow of an adequate supply of blood through the cardiovascular system. These heart valves can be rendered less effective by congenital malformations, inflammatory processes, infectious conditions, or disease. Such damage to the valves can result in serious cardiovascular compromise or death.

For many years the definitive treatment for such disorders was the surgical repair or replacement of the valve during open heart surgery. However, such surgeries are highly invasive, and are prone to many complications. Therefore, elderly and frail patients with defective heart valves often went untreated. More recently, transcatheter techniques have been developed for introducing and implanting prosthetic devices in a manner that is much less invasive than open heart surgery. Such transcatheter techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle.

The mitral valve has a very different anatomy than other native heart valves. The mitral valve includes an annulus portion, which is an annular portion of the native valve tissue surrounding the mitral valve orifice, and a pair of cusps or leaflets extending downward from the annulus into the left ventricle. The mitral valve annulus can form a "D" shaped, oval, or otherwise out-of-round cross-sectional shape having major and minor axes. FIG. 1 shows a normal mitral valve having a posterior leaflet and an anterior leaflet. The anterior leaflet can be larger than the posterior leaflet, forming a generally "C" shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords, called chordae tendineae, tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. There are many different causes of mitral regurgitation. One particular cause is excessive slack in at least one of the native leaflets and/or chordae tendineae. This excessive slack prevents the native leaflets from effectively closing during the systolic phase of heart contraction, thus allowing mitral regurgitation. FIG. 2, for example, shows a fail posterior leaflet 10 that does not properly co-apt with the anterior leaflet 12 during systole. This condition typically is caused by excessive slack or failure of the chordae tendineae connected to the posterior leaflet.

In another case, the heart may have structural defects such that the leaflets are too far apart to provide sufficient coaptation of the leaflets to prevent flow to the left atrium during systole. In another case, the ventricle may be enlarged, pulling the leaflet coaptation edge away from the base too far below the annular plane towards the apex of the heart, preventing proper coaptation of the leaflets.

Various devices and methods for treating mitral regurgitation have been developed, including implanting a prosthetic valve within the native mitral valve, surgically removing a portion of one or both of the native heart valve leaflets to reduce excessive slack, or clipping, suturing or otherwise coupling the leaflets to each other to improve coaptation. These devices and methods can, however, be highly invasive, require lengthy or complex procedures, or require an extensive recovery period.

Thus, there is a continuing need for improved devices and methods for repairing native heart valve leaflets.

SUMMARY

Described herein are embodiments of devices that are primarily intended to be used to repair the native leaflets of the mitral, aortic, tricuspid, or pulmonary heart valve, as well as methods for repairing the same. The devices can be used to remove excess slack in a native heart valve leaflet by folding or plicating the native leaflet.

In one representative embodiment, an apparatus for repairing a heart valve comprises a leaflet-plicating mechanism configured to plicate a leaflet of a heart valve and a helical needle comprising a plurality of coils. The needle is configured to implant a suture to extend helically through plicated tissue of the heart valve.

In some embodiments, the leaflet-plicating mechanism comprises first and second leaflet-capture arms, which can be configured to move toward and away from each other between an open position and closed position. The leaflet-capture arms can be configured to plicate the leaflet as the leaflet-capture arms are moved from the open position to the closed position.

In some embodiments, each of the first and second leaflet-capture arms can comprise a shaft and a leaflet-engaging member disposed in the shaft and having a distal end portion configured to form a hook when deployed from the shaft to extend around a free edge of the leaflet.

In some embodiments, the distal end portion of each leaflet-engaging member can be retained in a substantially linear state inside the corresponding shaft and can deflect to a deformed shape under its own resiliency to form the hook when deployed from the corresponding shaft.

In some embodiments, the apparatus further comprises a catheter having an elongated shaft, the shaft having first and second lumens, the leaflet-plicating mechanism configured to extend through the first lumen and the needle configured to extend through the second lumen.

In some embodiments, the apparatus further comprises a catheter having an elongated shaft, the shaft having a lumen having a substantially C-shaped profile in a plane perpendicular to a longitudinal axis of the shaft, each of the leaflet-capture arms disposed in the lumen and having a substantially C-shaped cross-sectional profile in a plane perpendicular to the longitudinal axis of the shaft.

In some embodiments, the leaflet-engaging members are made of Nitinol.

In some embodiments, the apparatus further comprises one or more actuators configured to move the first and second leaflet-capture arms between the closed and open positions.

In some embodiments, the apparatus further comprises a biasing member configured to bias the first and second leaflet-capture arms to one of the closed or open positions.

In some embodiments, the apparatus further comprises a suture and a suture anchor secured to an end of the suture, the suture and the suture anchor configured to be deployed from the needle to form stitching extending through the plicated tissue.

In some embodiments, the suture anchor is compressible to a compressed state for delivery in a lumen of the needle and expandable to an expanded state when deployed from the needle.

In another representative embodiment, a method for repairing a heart valve comprises inserting a leaflet-plicating mechanism into a heart of a patient; plicating a leaflet of the heart valve with the leaflet-plicating mechanism; inserting a needle into the heart; inserting a helical portion of the needle through plicated tissue of the leaflet; and deploying a suture from the needle to form a helically extending stitch extending through the plicated tissue.

In some embodiments, plicating the leaflet comprises engaging the leaflet with first and second leaflet-capture arms of the leaflet-plicating mechanism and moving the first and second leaflet-capture arms toward each other to plicate the leaflet between the first and second leaflet-capture arms.

In some embodiments, engaging the leaflet with the first and second leaflet-capture arms comprises deploying leaflet-engaging members from respective shafts of the first and second leaflet-capture arms, and placing distal end portions of the leaflet-engaging members around a free edge of the leaflet.

In some embodiments, when the leaflet-engaging members are deployed from respective shafts of the first and second leaflet-capture arms, the distal end portions of the leaflet-engaging members form hooks that are placed around the free edge of the leaflet.

In some embodiments, the method further comprises deploying a suture anchor from the needle, the suture anchor being secured to a distal end of the suture.

In some embodiments, the suture anchor expands when deployed from the needle.

In some embodiments, the leaflet-plicating mechanism and the needle are advanced through the patient's vasculature to the heart.

In some embodiments, the leaflet is a mitral valve leaflet.

In some embodiments, the method further comprises placing a suture clip on the suture.

The foregoing and other objects, features, and advantages of the invention will become more apparent from the following detailed description, which proceeds with reference to the accompanying figures.

BRIEF DESCRIPTION OF THE DRAWINGS

FIG. 5A is a perspective view of a leaflet-capture mechanism of the repair apparatus, according to one embodiment.

FIG. 5B is a cross-sectional view of one of the leaflet-capture arms of the leaflet-capture mechanism taken along line 5B-5B of FIG. 5A.

FIG. 5C is a cross-sectional view of the other leaflet-capture arm of the leaflet-capture mechanism taken along line 5C-5C of FIG. 5A.

FIGS. 17-22 show a method of implanting a suture in the plicated tissue using the needle of FIG. 7, according to one embodiment.

DETAILED DESCRIPTION

Figure 1:
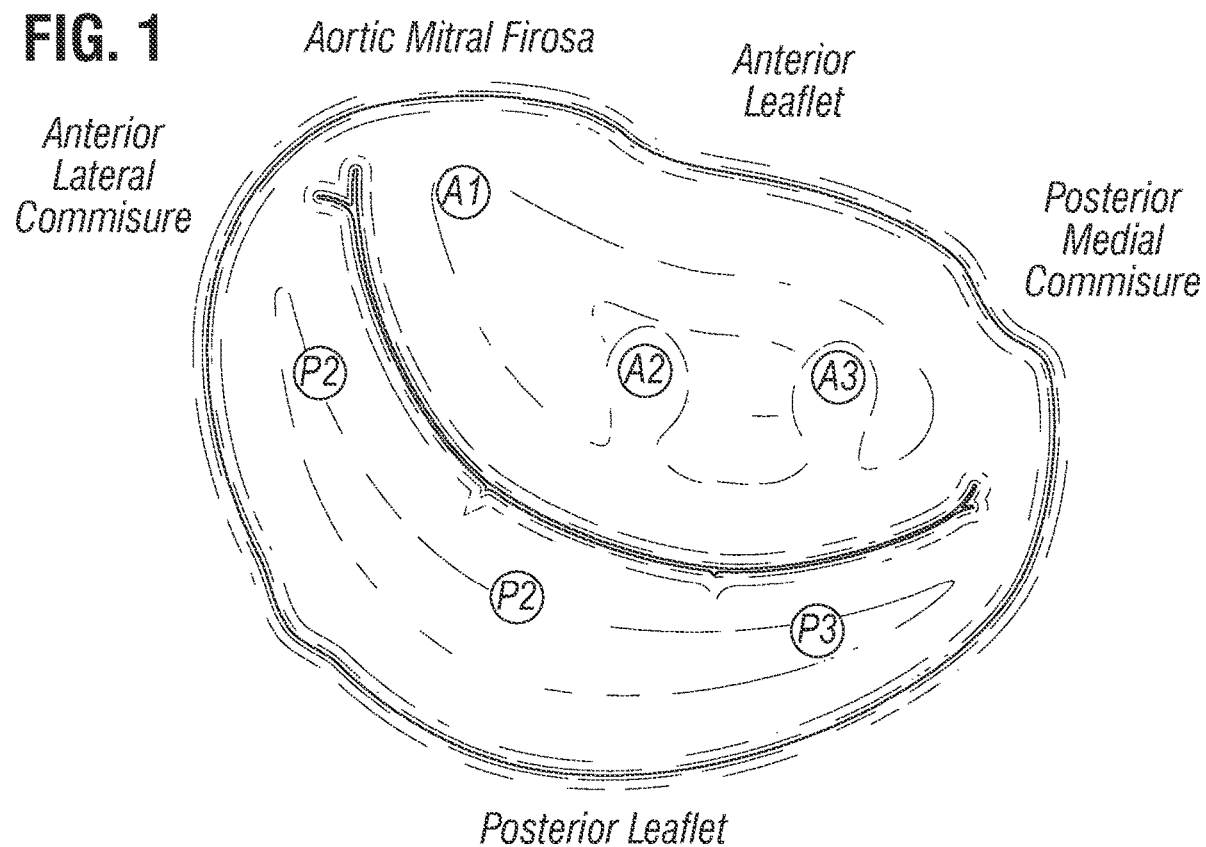
FIG. 1 is a plan view of a normal mitral valve.
Figure 2:
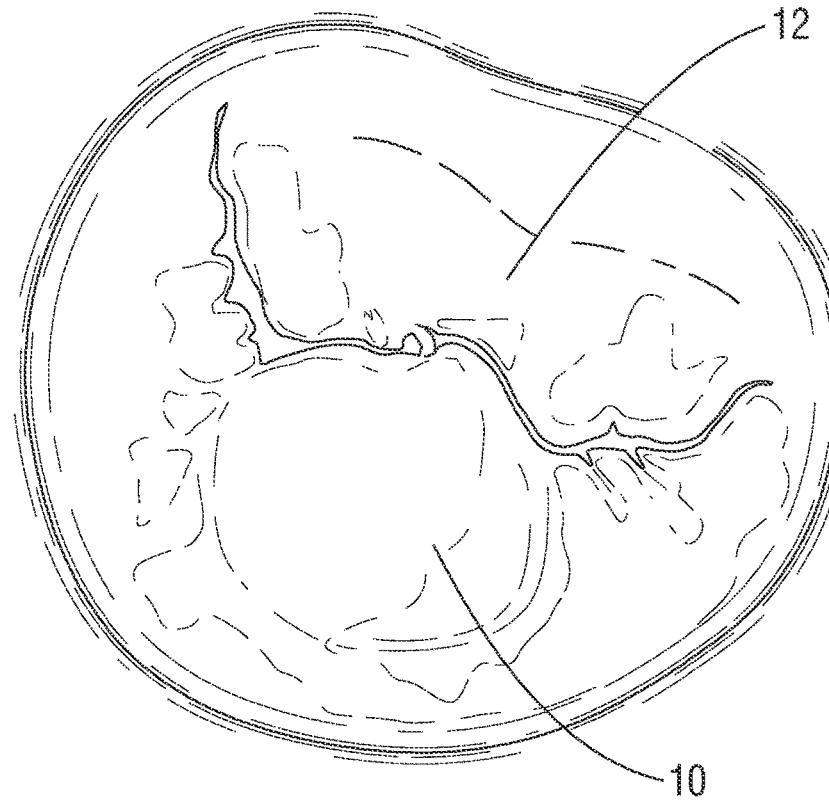
FIG. 2 is a plan view of a mitral valve having a fail posterior leaflet.

Described herein are embodiments of devices that are primarily intended to be used to repair the native leaflets of the mitral, aortic, tricuspid, or pulmonary heart valve, as well as methods for repairing the same. The devices can be used to remove excess slack in a native heart valve leaflet by folding or plicating the native leaflet. By removing the excessive slack in the native leaflet, these devices can reduce or improve valvular regurgitation and, thus, improve the functionality of a defective native heart valve. In particular embodiments, a heart valve repair apparatus can be configured to repair a native mitral valve leaflet. The apparatus can access the mitral valve from the left ventricle and/or the left atrium in a minimally invasive manner (e.g., using a transcatheter technique). In particular embodiments, the repair apparatus can be used to repair a leaflet on a beating heart without open-heart surgery and cardiopulmonary bypass in an off-pump procedure.

FIGS. 3-7 shows a transcatheter leaflet repair apparatus 14 for repairing a prolaptic heart valve leaflet, such as by plicating a heart valve leaflet. The repair apparatus 14 is described in the present application in the context of repairing a prolaptic mitral valve leaflet, although it should be understood that the apparatuses and methods disclosed herein also can be used to repair leaflets of the other native valves of the heart (i.e., the aortic valve, the pulmonary valve and the tricuspid valve). In some embodiments, the apparatuses and methods disclosed herein can be used to repair a prosthetic leaflet or other components of a prosthetic heart valve.

The repair apparatus 14 in the illustrated embodiment generally comprises an outer catheter 16, a leaflet-capture mechanism 18 (also referred to as a leaflet-grabbing mechanism or leaflet-plicating mechanism), and a helical sewing needle 20. The outer catheter 16 can comprise an elongated shaft 24 extending from a handle 46. The shaft 24 can comprise one or more lumens for receiving other components of the repair apparatus 20. For example, the shaft 24 can comprise a central lumen 26 for receiving the needle 20 (FIG. 7) of the repair apparatus and an outer lumen 30 for receiving leaflet-capture arms 32, 34 (FIG. 5) of the leaflet-capture mechanism 18. The outer lumen 30 desirably is curved in a cross-sectional plane perpendicular to the longitudinal axis of the shaft 24, such as having a C-shaped cross-section as best shown FIG. 3, or is otherwise sized and shaped to allow lateral or side-to-side movement of the leaflet-capture arms 32, 34 relative to each other within the lumen 30, as further described below. The leaflet-capture arms 32, 34 are configured to capture and plicate a heart valve leaflet while the needle 28 is used to suture the plicated tissue, as described in detail below. As shown in FIG. 4, the central lumen 26 can have internal threads 36 along a distal end portion thereof corresponding to coils of the needle 28.

Figure 3:
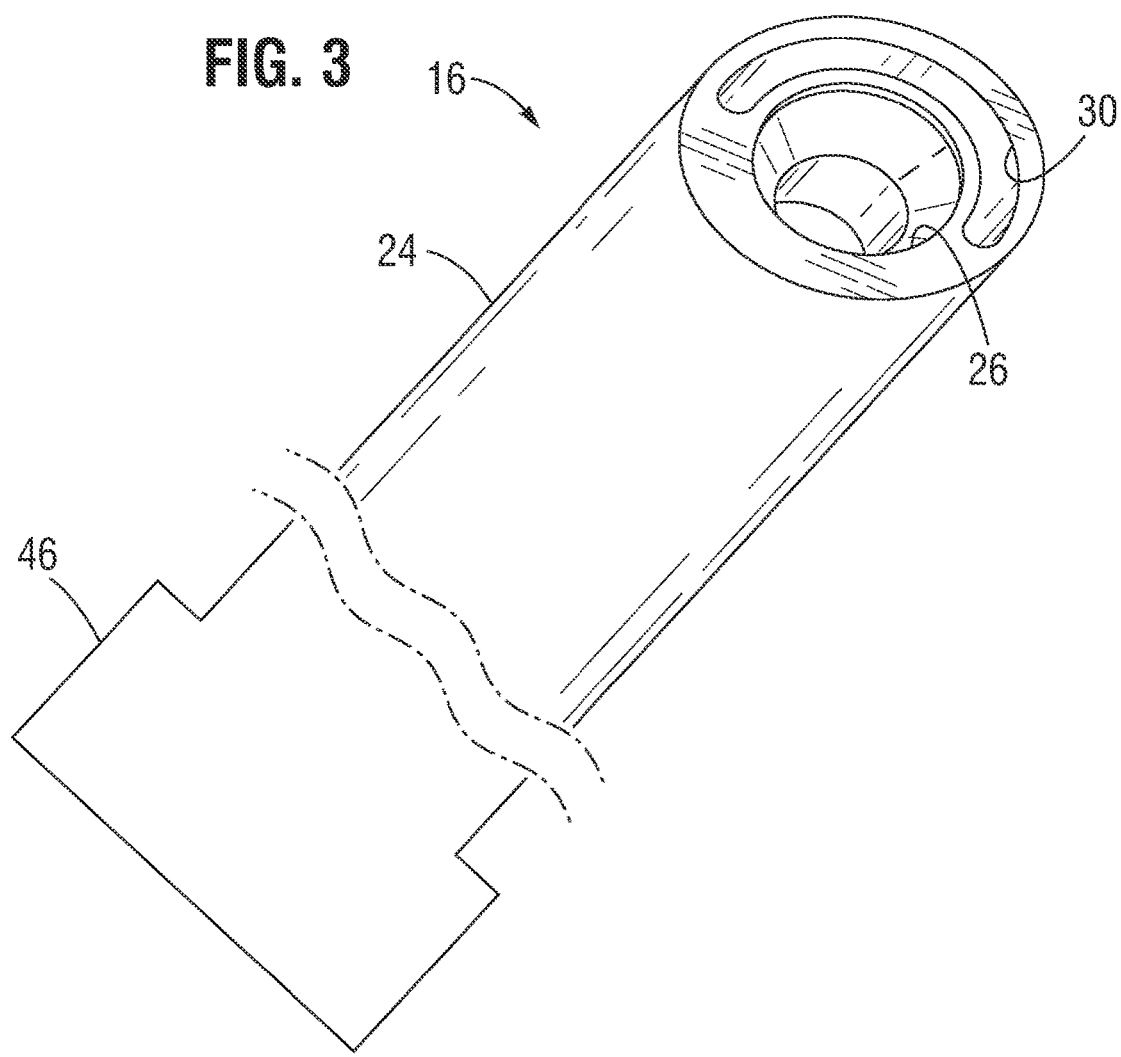
FIG. 3 is a perspective view of an outer catheter of a leaflet repair apparatus, according to one embodiment.
Figure 4:
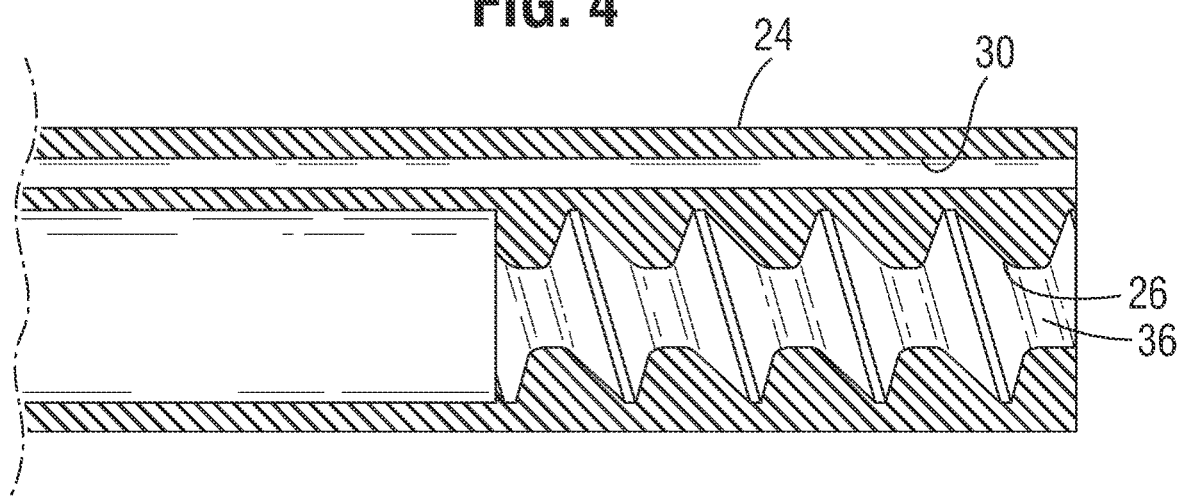
FIG. 4 is a cross-sectional view of the catheter of FIG. 3 taken along a longitudinally extending plane through the catheter.

As shown in FIG. 3, the handle 46 of the outer catheter 16 can be coupled to the proximal end of the shaft 24. The handle 46 can have one or more actuators or control knobs to control various functions of the repair apparatus 20. For example, the handle 46 can include a steering mechanism operatively connected to one or more pull wires extending through the shaft 24. Actuating the steering mechanism can adjust the tension in the one or more pull wires to adjust the curvature of the shaft 24 to facilitate steering of the shaft through a patient's vasculature. Further details of a catheter construction having a steering mechanism and one or more pull wires are disclosed in U.S. Publication Nos. 2008/0065011 and 2009/0281619, which are incorporated herein by reference.

The leaflet-capture mechanism 18 is configured to remove excess slack in a native heart valve leaflet (e.g., a prolaptic leaflet) by plicating or folding a portion of the leaflet. As noted above, the leaflet-capture mechanism 18 in the illustrated embodiment comprises two leaflet-capture arms 32, 34. Referring to FIG. 5A, each of the leaflet-capture arms 32, 34 can comprise a shaft 38 and a leaflet-engaging member 40 extending through a lumen 42 of a respective shaft 38. The leaflet-engaging member 40 can be in the form of, for example, a flexible wire or needle, having a pre-curved distal end portion 44. Each shaft 38 can have a curved shape or profile in a cross-sectional plane perpendicular to its longitudinal axis. For example, as best shown in FIGS. 5B and 5C, each shaft 38 can have a C-shaped cross-sectional profile corresponding to the shape of the lumen 30 to facilitate lateral movement of the shafts 38 within the lumen 30. The curved shape of the lumen 30 also causes the leaflet-capture arms 32, 34 to move along a curved path around the longitudinal axis of the shaft 24.

The leaflet-capture arms 32, 34 are configured to be moved toward and away from each other between an open position (see FIG. 6A) for receiving a portion of a leaflet between the arms and a closed position (FIG. 6C) for retaining the leaflet portion between the arms. The leaflet-capture mechanism 18 can include a biasing member 48 (FIG. 5A) configured to bias the leaflet-capture arms 32, 34 away from each other to a normally open position. The biasing member 48 can comprise, for example, any of various types of springs (e.g., a U-shaped spring as shown, a coil spring, a torsion spring, etc.) or an elastomeric component positioned between the leaflet-capture arms 32, 34.

The leaflet-capture mechanism 18 also can include first and second actuators 50, 52, respectively, configured to move the leaflet-capture arms 32, 34 toward each other against the bias of the biasing member 48. The first actuator 50 can extend through the shaft 38 of the first arm 32, laterally through an opening in the shaft of the first arm, and into the shaft 38 of the second arm 34. The first actuator 50 can have an enlarged distal end portion 54 captured or otherwise connected to the shaft 38 of the second arm 34. Similarly, the second actuator 52 can extend through the shaft 38 of the second arm 34, laterally through an opening in the shaft of the first arm, and into the shaft 38 of the first arm 32. The second actuator 52 can have an enlarged distal end portion 56 captured or otherwise connected to the shaft 38 of the first arm 32. The first and second actuators 50, 52 can be formed from, for example, relatively stiff metal wires.

The first actuator 50 can be manipulated to draw or move the second leaflet-capture arm 34 toward the first leaflet-capture arm 32 in the direction of arrow 58, such as by applying a proximally directed force to the first actuator 50 in the direction of arrow 60. Likewise, the second actuator 52 can be manipulated to draw or move the first leaflet-capture arm 32 toward the second leaflet-capture arm 34 in the direction of arrow 59, such as by applying a proximally directed force to the second actuator 52 in the direction of arrow 60. The first and second actuators 50, 52 can be slidable within the shafts 38 of the first and second leaflet-capture arms 32, 34, respectively, such that pulling the first and second actuators 50, 52 proximally is effective to move the shafts 38 toward each other.

Each of the actuators 50, 52 can extend the length of the shafts 38 and can have proximal end portions that can be manipulated by a user to move the leaflet-capture arms 32, 34. For example, the proximal end portions of the actuators 50, 52 can extend beyond the handle 46 and can be exposed for engagement with the hands of the user. In other embodiments, the proximal end portions of the actuators 50, 52 can be operatively connected to a common actuator or control knob on the handle 46 or to respective actuators or control knobs on the handle 46 configured to move the actuators. Upon actuation of the actuators 50, 52, the shafts 38 can slide toward each other within the lumen 30 of the shaft 24 from the open position (FIGS. 5A and 6A) to the closed position (FIG. 6C). Upon release of force from the actuators 50, 52, the shafts 38 are pushed away from each other under the biasing force of the biasing member 48 from the closed position to the open position.

In an alternative embodiment, the biasing member 48 can be operable to bias the leaflet-capture arms 32, 34 to the closed position (FIG. 6C) and the first and second actuators 50, 52 can be operable to move the leaflet-capture arms 32, 34 from the closed position to the open position against the biasing force of the biasing member 48.

The leaflet-engaging members 40 can be slidable axially and rotatable within respective lumens 42 of the shafts 38. The distal end portions 44 of the leaflet-engaging members 40 can be disposed within the lumens 42 when the leaflet-capture mechanism 18 is advanced into the heart to perform a procedure. At the desired location within the heart, each of the leaflet-engaging members 40 can be advanced distally to deploy its distal end portion 44 from a respective shaft 38, causing the distal end portion 44 to assume the deflected state shown in FIG. 5A. In the deflected state, the distal end portion 44 desirably curves back toward the respective shaft 38 so as to form a hook that can extend around and engage a free edge of a native leaflet. When both distal end portions 44 are positioned around the free edge of the leaflet, moving the first and second leaflet-capture arms 32, 34 toward each other is effective to plicate or form one or more folds in the portion of the leaflet captured between the arms 32, 34.

Each leaflet-engaging member 40 can extend the length of its respective shaft 38 and can have a proximal end portion that extends proximally beyond the proximal end of its respective shaft 38 and/or the handle 46 for manipulation by a user. In particular embodiments, the proximal end portions of the leaflet-engaging members 40 can be operatively connected to a common actuator or control knob on the handle 46 or to respective actuators or control knobs on the handle 46 configured to move the actuators.

In alternative embodiments, other types of leaflet-capture mechanisms can be used. For example, the leaflet-capture mechanism can include more than two leaflet-capture arms to facilitate the forming of folds in the leaflet. In another implementation, the leaflet-capture mechanism can be configured to fold a leaflet by placing a section of a leaflet between two or more arms of the leaflet-capture mechanism and rotating the arms, as disclosed in U.S. Publication No. 2016/0287383, which is incorporated herein by reference.

Figure 7:
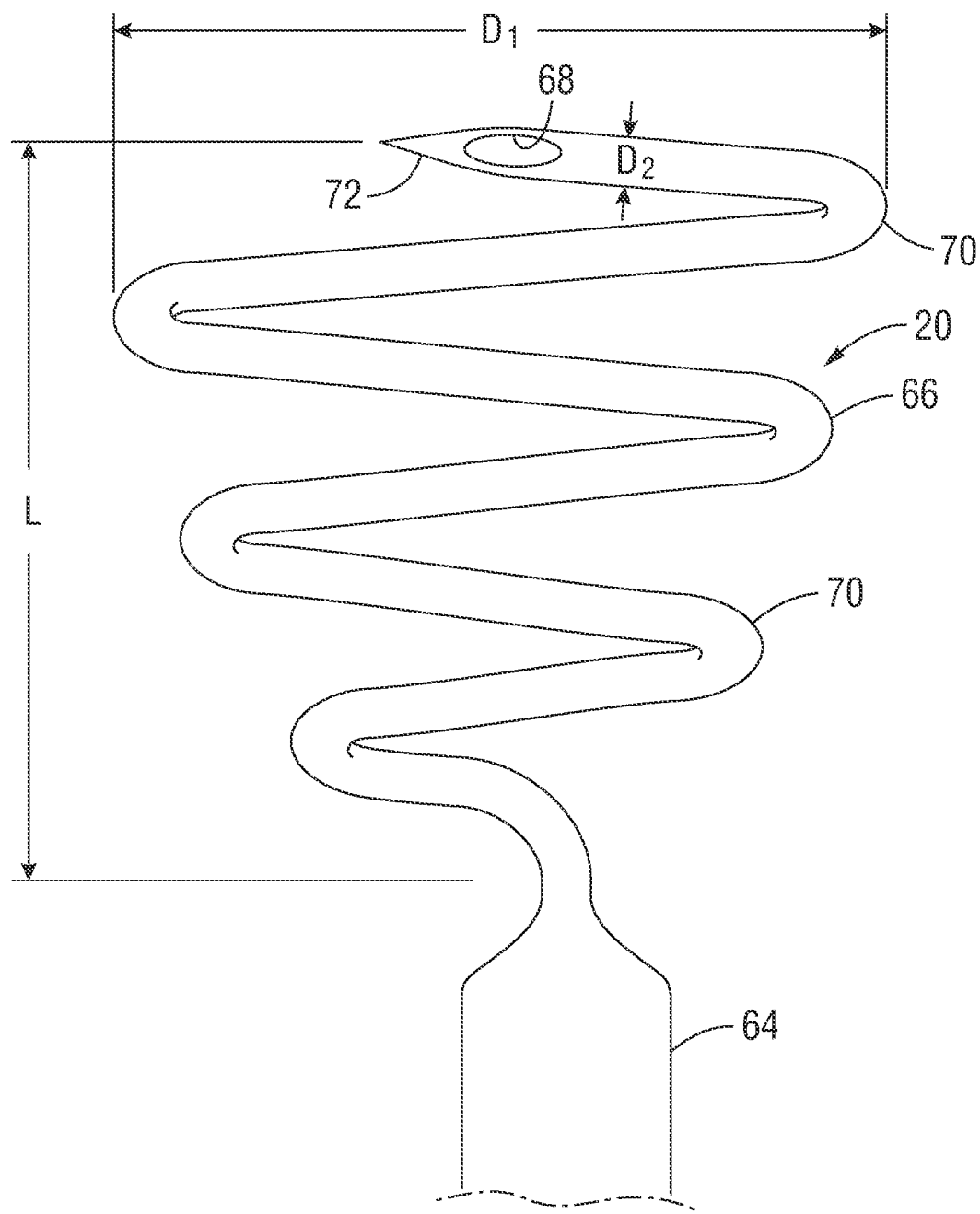
FIG. 7 is an enlarged side view of the distal end portion of a helical needle of the repair apparatus, according to one embodiment.

Referring to FIG. 7, the needle 20 can comprise an elongated shaft 64, a helical portion 66 extending from the distal end of the shaft 64, and a lumen 68 extending through the helical portion 66 and the shaft 64. The helical portion 66 can comprise a plurality of coils 70, which can increase in diameter moving in a direction from the shaft 64 toward a distal end portion 72 of the helical portion 66. In other embodiments, each coil 70 can have the same diameter. In still other embodiments, the helical portion 66 can have smaller-diameter coils at opposite ends of the helical portion and larger-diameter coils intermediate the ends (such as shown in FIG. 15).

The distal end portion 72 can taper to a pointed or sharp tip to more easily penetrate tissue. In certain embodiments, the helical portion 66 can be relatively more flexible than the shaft 64. The shaft 64 can extend through the lumen 26 the entire length of the shaft 24 and can have a proximal end portion that extends proximally beyond the handle 46 for manipulation by a user. In particular embodiments, the proximal end portion of the shaft 64 can be operatively connected to an actuator or control knob on the handle 46 configured to move the needle 20 axially and rotationally relative to the shaft 24 to deploy the helical portion 66 from the shaft 24. During delivery into the body, the helical portion 66 can be disposed in the internally threaded portion 36 of the lumen 26. The helical portion 66 threadably engages the internal threads such that rotation of the shaft 64 causes the helical portion to move axially and rotational relative to the shaft 24.

In an alternative embodiment, the shaft 64 can be operatively connected to a lead screw or equivalent mechanism in the handle 46 to produce axial and rotational movement of the needle 70 relative to the shaft 24. In such an embodiment, the lumen 26 need not include internal threads to produce rotational movement of the needle.

Figure 15:
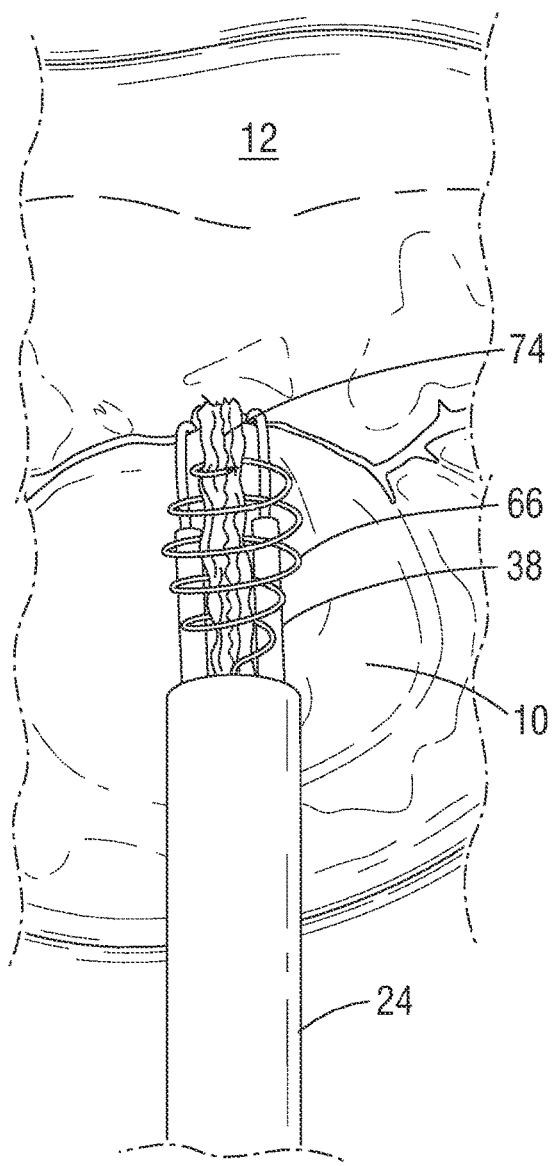

As the needle 70 is deployed from the distal end of the shaft 24 while rotating, the helical portion 66 passes through the plicated section of leaflet tissue captured between the leaflet-capture arms 32, 34, as depicted in FIG. 15. The folds of the plicated tissue can be sutured to each other with a suture 80 (FIGS. 16A and 16B) deployed from the needle, as described in greater detail below.

In particular embodiments, the helical portion 66 can have an overall length L of about 6 mm to about 18 mm, with about 12 mm being a specific example. The diameters of the coils 70 can vary from about 4 mm to about 12 mm. In certain implementations, the maximum diameter $D_1$ of the coils 70 is about 8 mm. The diameter $D_2$ of the tubing that forms the helical portion 66 can be about 0.5 mm to about 1.0 mm, with about 0.7 mm being a specific example. Of course, these specific dimensions (as well as other dimensions provided in the present specification) are given to illustrate the invention and not to limit it. The dimensions provided herein can be modified as needed in different applications or situations.

In use, the repair apparatus 14 can be introduced into a patient's vasculature (e.g., via a femoral artery, a femoral vein or other suitable access point) and percutaneously advanced to the patient's heart using any of various delivery techniques. In a transfemoral procedure, the repair apparatus can be inserted through a femoral artery and the aorta to the heart in a retrograde direction (typically, but not exclusively used for performing a procedure on the leaflets of the aortic or mitral valves). Similarly, the repair apparatus can be inserted through a femoral vein and the vena cava to the right side of the heart in an antegrade direction (typically, but not exclusively used for performing a procedure on the leaflets of the pulmonary or tricuspid valves). In a transventricular procedure, the repair apparatus can be inserted through a surgical incision made in the chest and on the bare spot on the lower anterior ventricle wall (typically, but not exclusively used for performing a procedure on the leaflets of the aortic or mitral valves). Similarly, the repair apparatus can be inserted through a surgical incision on the wall of the right ventricle to access the pulmonary or tricuspid valves. In a transatrial procedure, the repair apparatus can be inserted through a surgical incision made in the wall of the left or right atrium to access the native valves on the left or right sides, respectively, of the heart. In a transaortic procedure, the repair apparatus can be inserted through a surgical incision made in the ascending aorta and advanced toward the heart (typically, but not exclusively used for performing a procedure on the leaflets of the aortic or mitral valves). In a trans-septal procedure, the repair apparatus can be advanced to the right atrium, such as via a femoral vein, and through the septum separating the right and left ventricles (typically, but not exclusively used for performing a procedure on the leaflets of the aortic or mitral valves). Further details of delivery techniques for accessing the native valves of the heart are disclosed in U.S. Patent Publication No. 2014/0067052, which is incorporated herein by reference.

Figure 8:
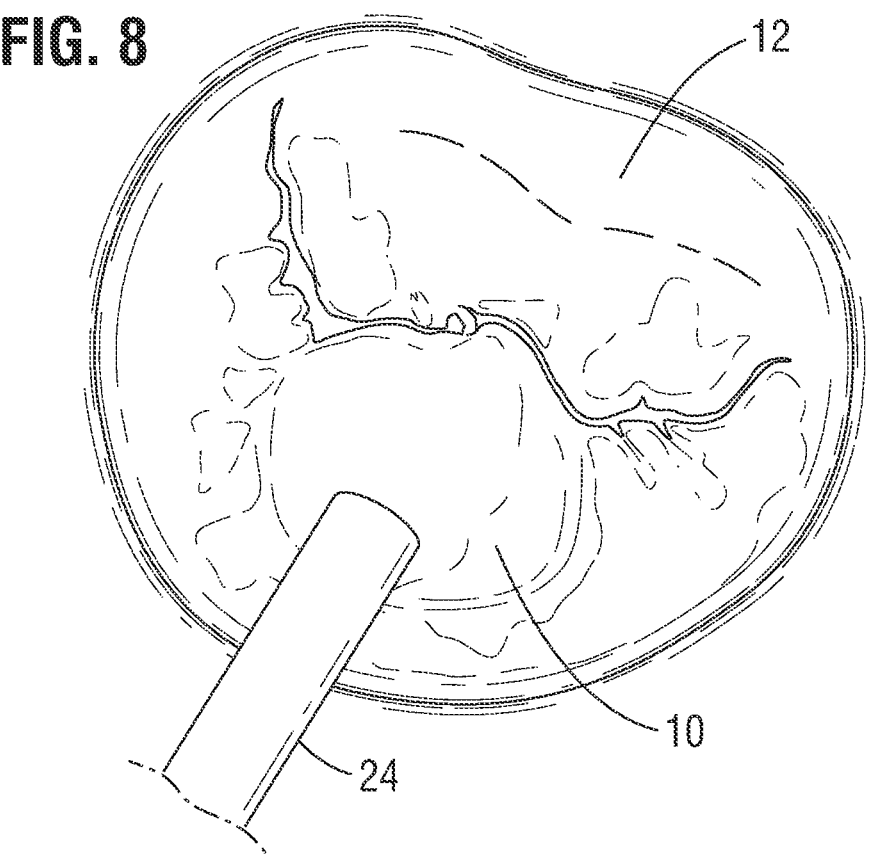
FIGS. 8-15 show a method of plicating a portion of a fail posterior mitral valve leaflet using the outer catheter of FIG. 3, the leaflet-capture mechanism of FIG. 5A, and the needle of FIG. 7, according to one embodiment.

FIGS. 8-22 illustrate use of the repair apparatus 14 for repairing a prolaptic posterior mitral valve leaflet 10. The repair apparatus 14 can be advanced into the heart via any of the delivery techniques described above. In the illustrated embodiment, the repair apparatus 14 is advanced into the left atrium (e.g., via a trans-septal approach) until the distal end portion of the shaft 24 is positioned adjacent the superior surface of the posterior leaflet 10, as shown in FIG. 8. In particular embodiments, the leaflet-capture mechanism 18 and the needle 20 can be pre-loaded within the shaft 24 of the outer catheter 16 and all three of these components are advanced together as a unit through the patient's vasculature. In other embodiments, the outer catheter 16 can be advanced through the patient's vasculature into the right atrium without the leaflet-capture mechanism 18 and the needle 20. Once the distal end portion of the shaft 24 is positioned adjacent the leaflet 10, the leaflet-capture mechanism 18 and the needle 20 can be advanced through the shaft 24 into the heart.

Figure 6A:
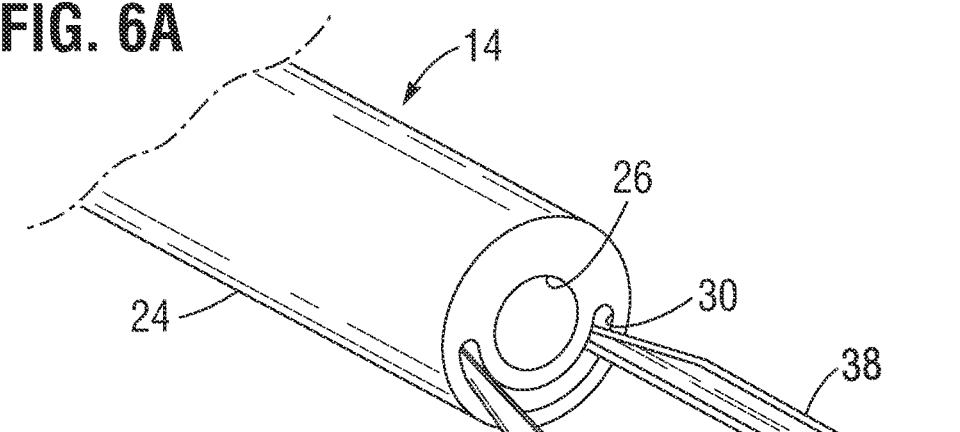
FIGS. 6A-6C show the leaflet-capture mechanism of FIG. 5A in various stages of deployment.
Figure 6B:
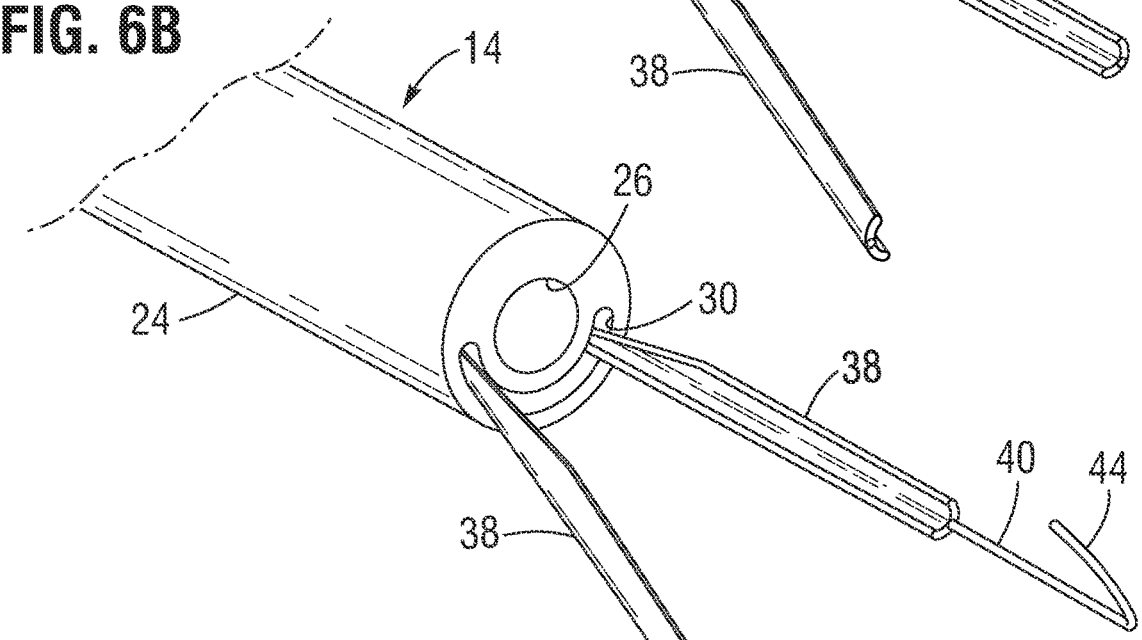
Figure 6C:
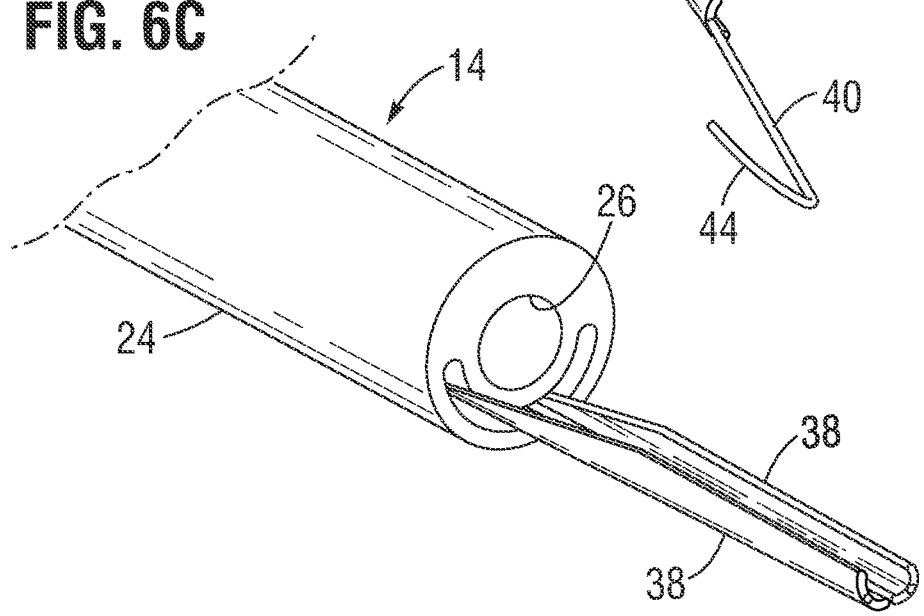
Figure 9:
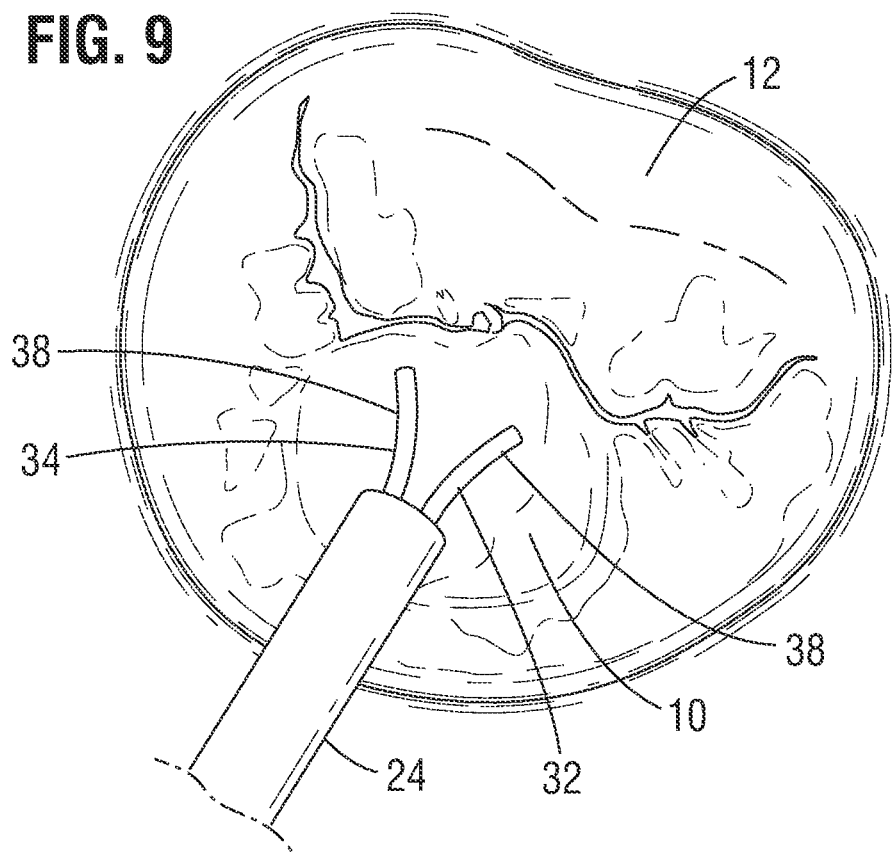
Figure 10:
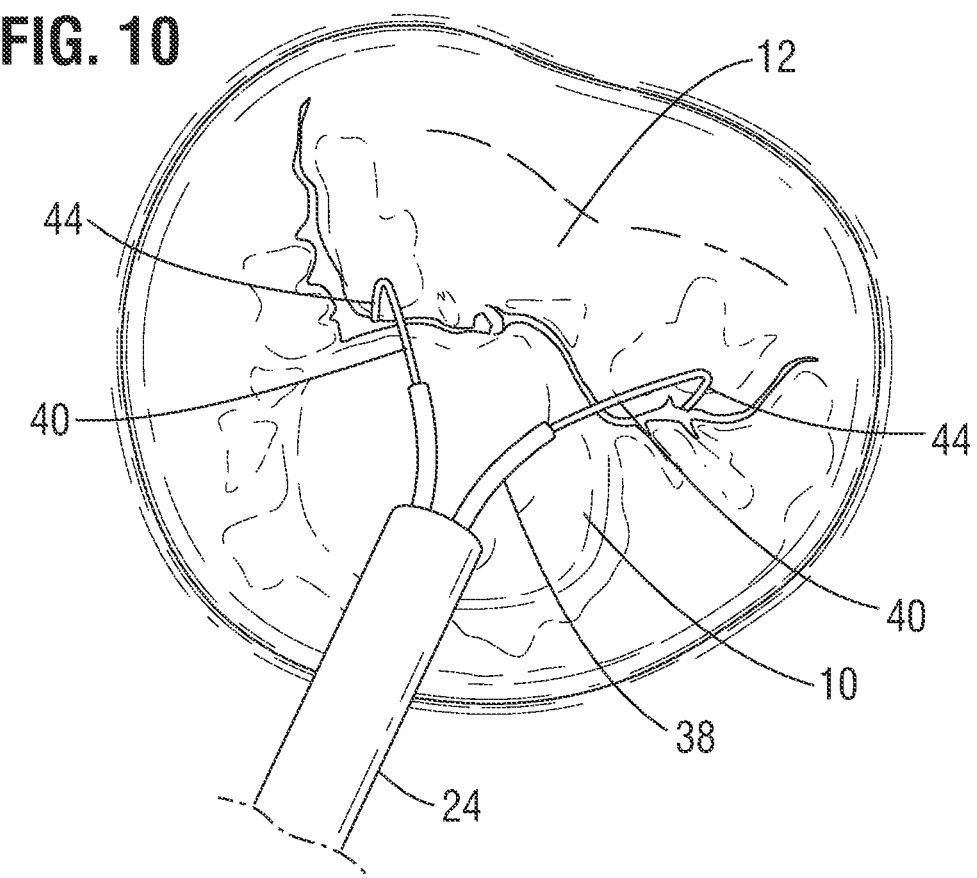

As shown in FIGS. 6A and 9, the shafts 38 of the first and second leaflet-capture arms 32, 34 can be advanced from the distal end of the shaft 24 across the superior surface of the posterior leaflet 10 and are placed in their open position. As shown in FIGS. 6B and 10, the leaflet-engaging members 40 can be advanced from the distal ends of their respective shafts 38, allowing the distal end portions 44 to deflect proximally to form hook portions at the distal ends of the leaflet-engaging members 40. The leaflet-engaging members 40 can be advanced distally so that their distal ends extend past the coaptation edge between the native leaflets 10, 12. If needed, the leaflet-engaging members 40 can be rotated relative to shafts 30 so that the distal ends of the hook portions 44 point toward the coaptation edge.

Figure 11:
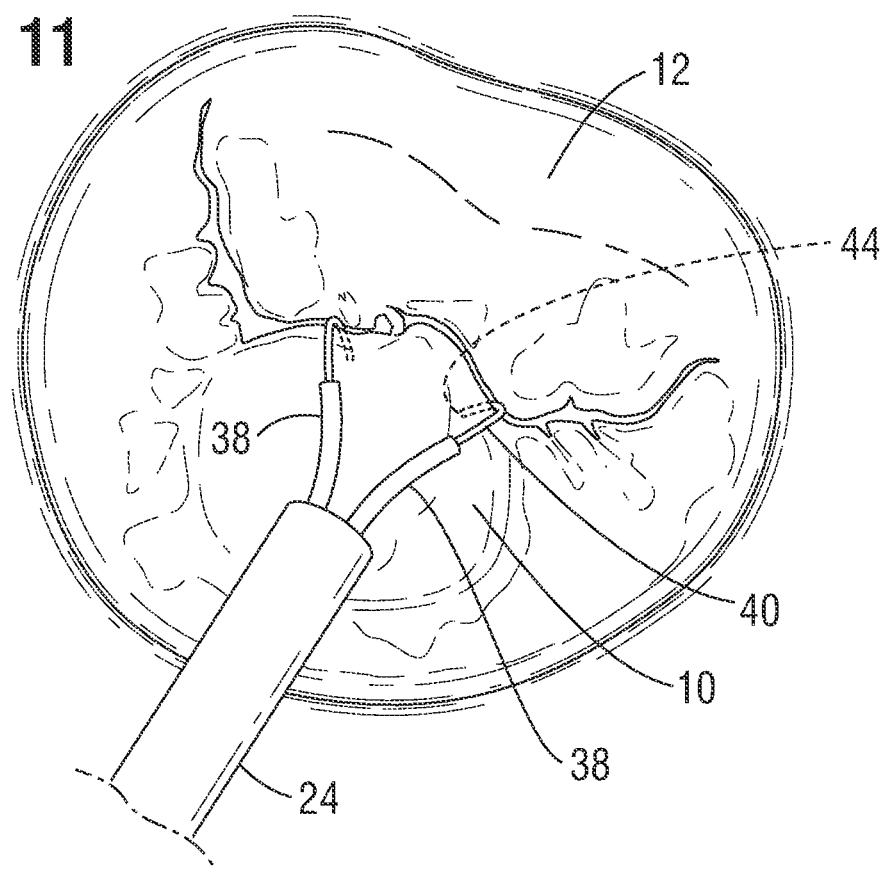
Figure 12:
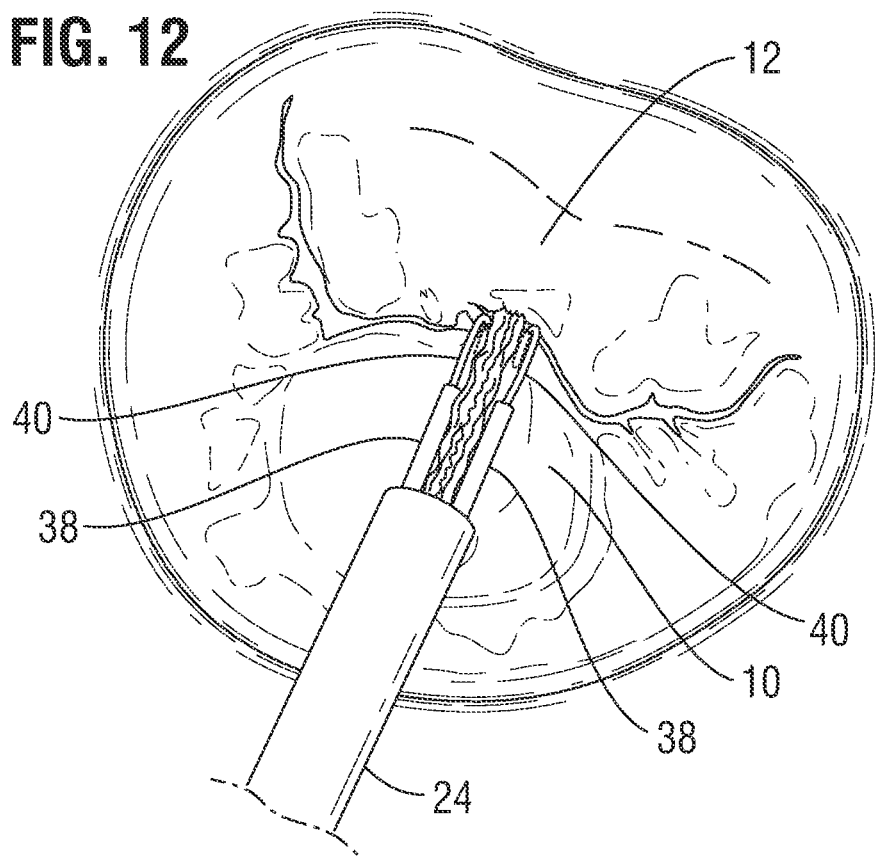

As shown in FIG. 11, the leaflet-engaging members 40 can then be retracted slightly such that the hook portions 44 extend around and engage the free edge of the posterior leaflet 10. The leaflet-engaging members 40 can be moved axially (distally and proximally) and rotationally relative to their respective shafts to place the hook portions 44 around the free edge of the posterior leaflet 10. As shown in FIG. 12, the shafts 38 of the leaflet-capture arms 32, 34 can then be moved toward each other to the closed position, causing the portion of the leaflet between the shafts 38 to "bunch up" or form one or more folds of tissue 74 between the shafts 38. Plicating the tissue in this manner removes excess slack from the leaflet 10, thereby improving coaptation with the anterior leaflet 12.

Figure 13:
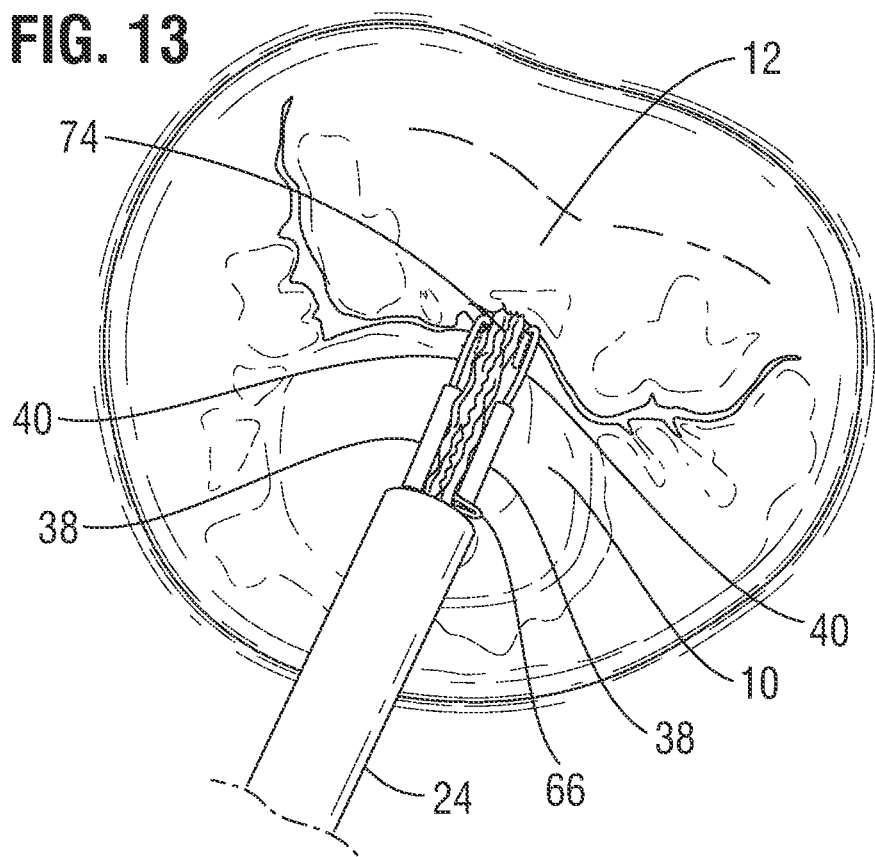
Figure 14:
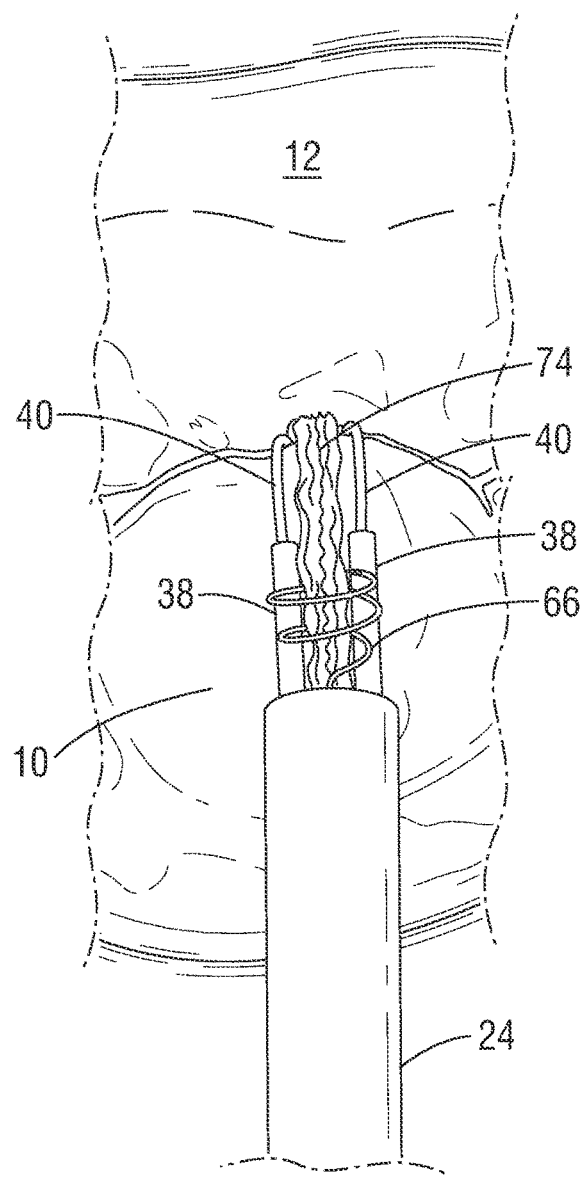

Referring now to FIGS. 13-15, the needle 20 can be advanced from the shaft 24 of the outer catheter 16. As the needle 20 is advanced distally, it also rotates around its longitudinal axis. In this manner, the distal end portion 72 of the helical portion 66 can penetrate the tissue 74 at several locations along the length of the tissue 74, allowing the helical portion 66 to extend helically through the tissue. Once the helical portion 66 forms a helical path through the tissue 74, a suture can be deployed from the needle to suture the folds of the tissue 74 together.

Figure 16A:
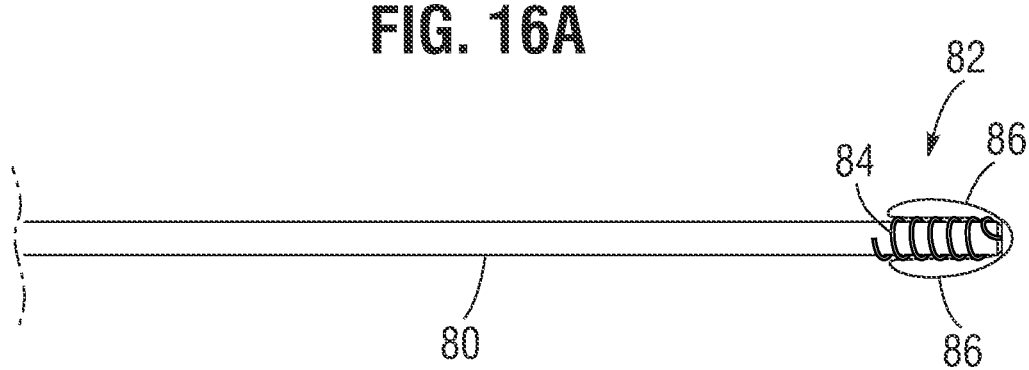
FIGS. 16A and 16B show an embodiment of a suture having a suture anchor at one end thereof.
Figure 16B:
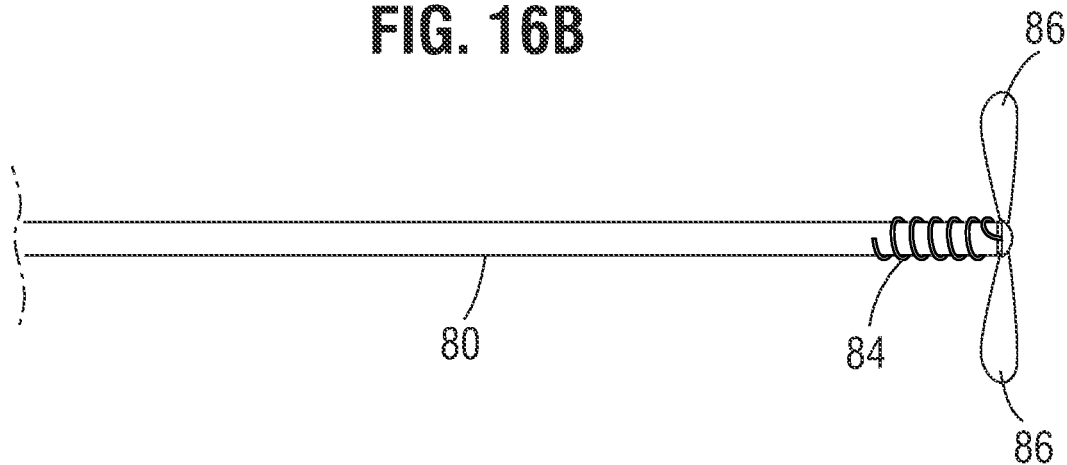

FIGS. 16A and 16B shows a suture 80 and a suture anchor 82 secured to a distal end portion of the suture, according to one embodiment. The suture anchor 82 is configured to anchor the distal end portion of the suture 80 to the tissue 74 when the suture 80 is deployed from the needle 20. In particular embodiments, the suture can comprise monofilament suture, for example, a polypropylene monofilament suture, having a diameter of about 0.4 mm. The anchor 82 can comprise a base 84 mounted to the distal end portion of the suture 80 and one or more radially expandable arms or wings 86. The base 84 can comprise, for example, a wire coil wrapped tightly around the distal end portion of the suture 80. Other techniques and mechanisms can be used to secure the anchor 82 to the suture, such as by tying the distal end portion of the suture to the anchor 82.

During delivery, the wings 86 can be folded inwardly to reduce the profile of the anchor and allow it to be loaded into the lumen 68 of the needle 20, as depicted in FIG. 16A. When deployed from the distal end of the needle 20, the wings 86 can radially expand under their own resiliency to a deployed state, as depicted in FIG. 16B. Although the anchor 82 in the illustrated embodiment includes two wings 86, in other embodiments, the anchor can have one wing 86 or more than two wings 86. The anchor 82, and in particular, the wings 86 can be formed from a shape-memory material, such as Nitinol. Other configurations for the suture anchor 82 are possible. For example, in another implementation, the anchor 82 can comprise an expandable/compressible piece of material that can expand in diameter or width when deployed from the needle 20. The expandable/compressible piece of material can comprise, for example, natural or synthetic sponge (e.g., polyurethane sponge), a foamed material made of a suitable polymer such as polyurethane or polyethylene, or any of various suitable elastomeric materials, such as polyurethane, silicon, polyolefins or a variety of hydrogels, to name a few.

Figure 17:
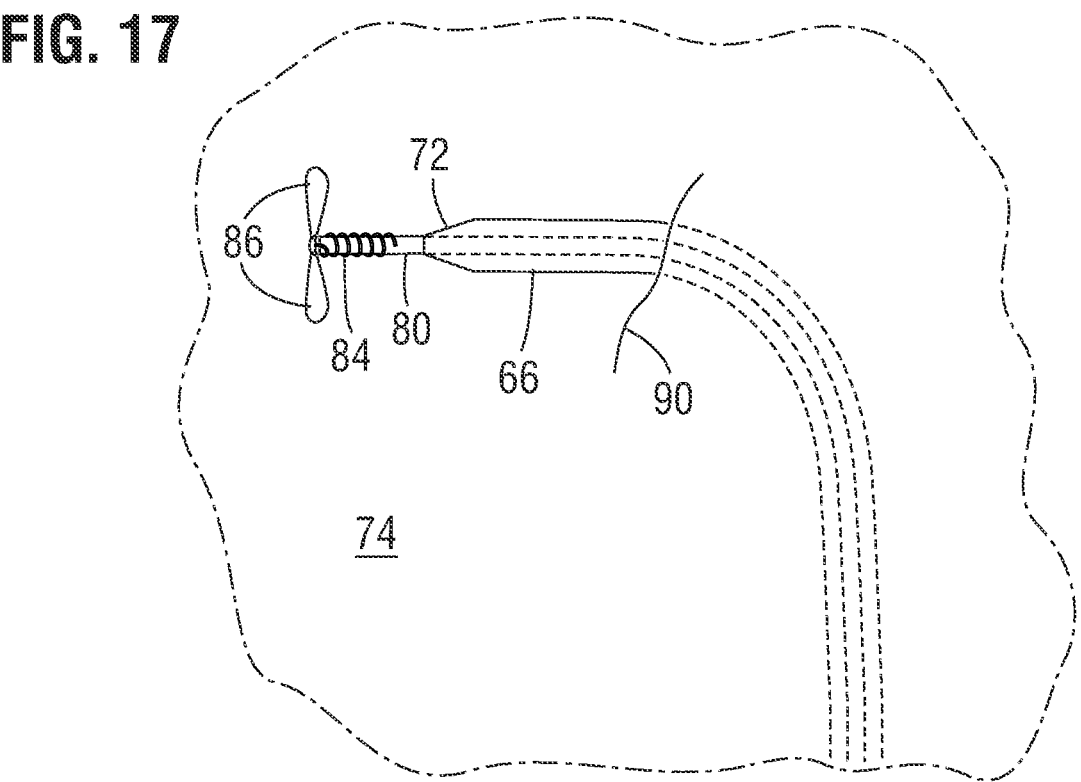

The suture 80 and the suture anchor 82 can be deployed from the needle 20 once the helical portion 66 is deployed to extend helically through the tissue 74. FIG. 17 is an enlarged view of the distal end portion of the helical portion 66 of the needle, showing the helical portion 66 extending through a puncture or slit 90 formed in the folded tissue 74 by the sharp distal end 72 of the helical portion near the coaptation edge of the leaflets 10, 12. As shown, the suture anchor 82 can be deployed from the distal end of the helical portion 66, which allows the wings 86 to expand to their deployed state substantially perpendicular to the length of the suture 80 and parallel to the surface of the tissue 74. The anchor 82 and the distal end portion of the suture 80 can be deployed from the needle 20 using various techniques and/or mechanisms. In one implementation, for example, the anchor 82 can be deployed from the needle 20 using hydraulic pressure of a pressurized fluid (e.g., saline) introduced into the lumen 68 of the needle. In another implementation, an elongated pusher member, such as in the form of a thin wire (e.g., similar to a guidewire) can be used to push the anchor 82 from the distal opening of the needle 20.

Figure 18:
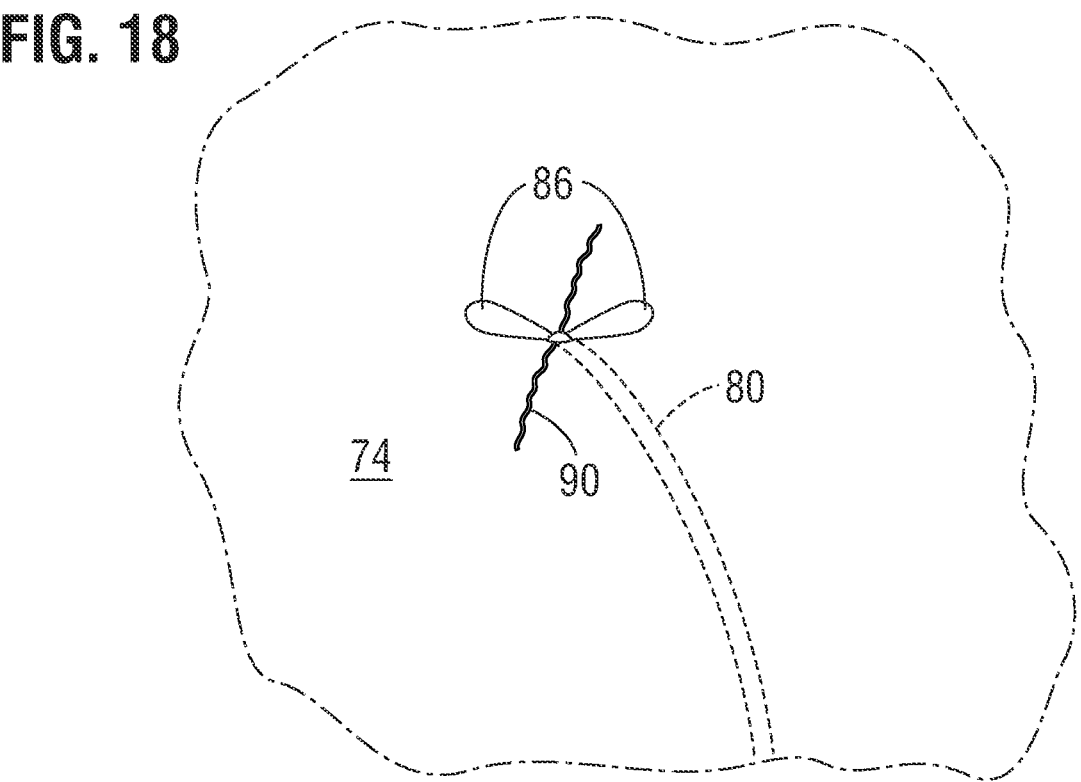
Figure 19:
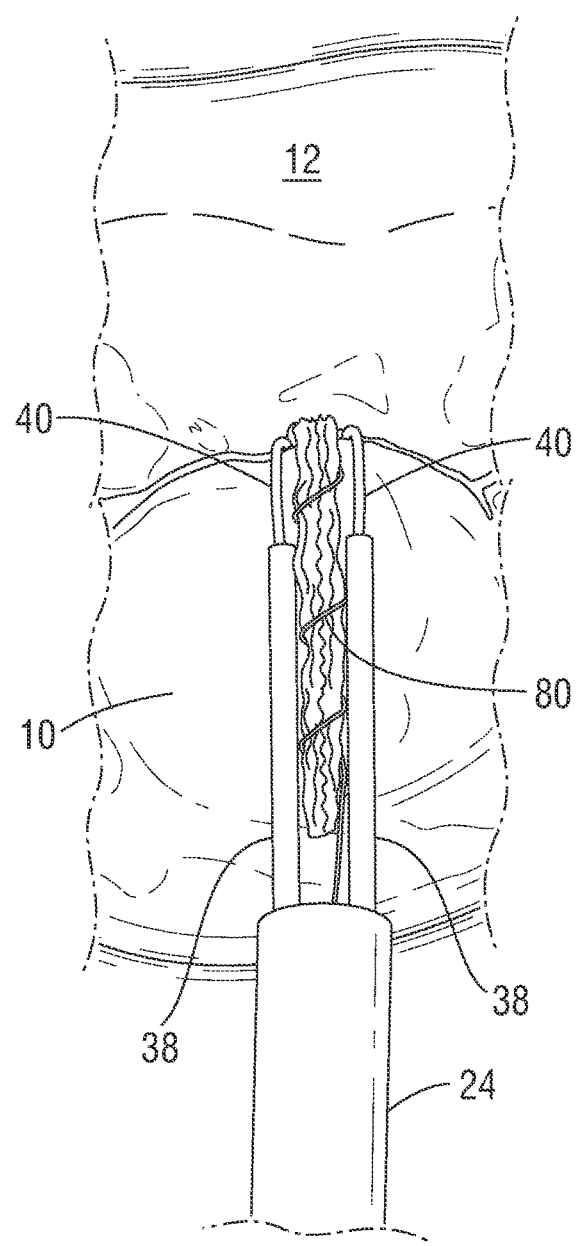
Figure 20:
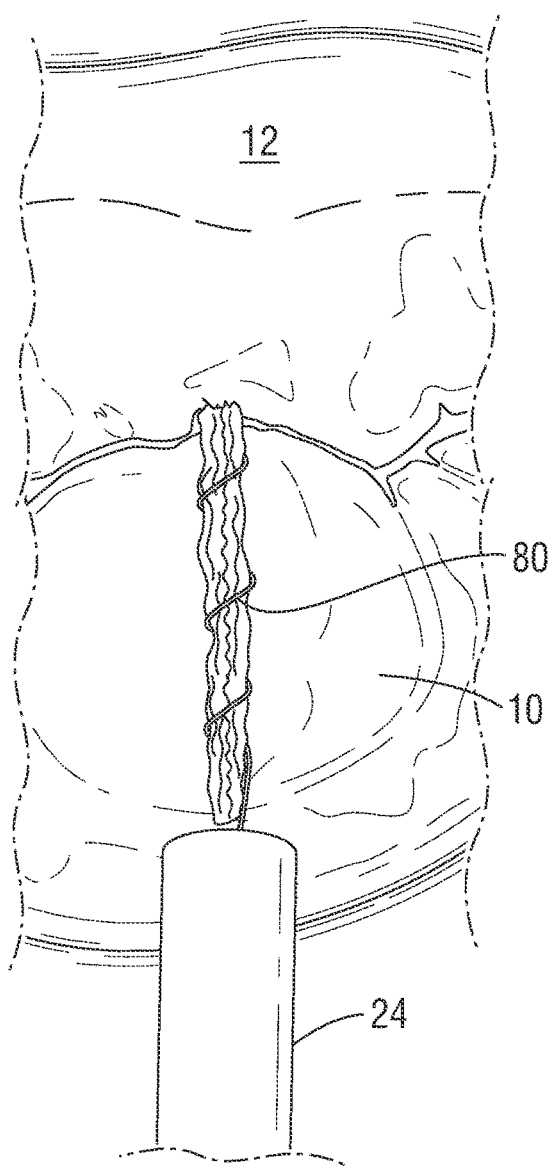

After deploying the anchor 82, the needle 20 can be retracted and removed from the heart (and from the patient's body if desired). As shown in FIG. 18, the suture 80 can be retracted until the wings 86 engage the tissue on opposite sides of the slit 90, retaining the distal end portion of the suture in place and resisting pull-through of the suture as it is tensioned. In some embodiments, the wings 86 can have barbs that can penetrate and anchor themselves to adjacent tissue to enhance the holding force of the anchor 82 against the adjacent tissue. As shown in FIG. 19, as the needle 20 is retracted, the suture 80 is left in place and forms a spiral or helical stitch extending along the tissue 74. After suturing the tissue 74, the leaflet-capture arms 32, 34 can be retracted back into the outer catheter 16 and optionally removed from the body, as shown in FIG. 20.

The suture 80 can be secured adjacent the annulus portion 92 of the leaflet 10 by a fastener 94. As shown in FIG. 21, the fastener 94 can be deployed from the shaft 24 using a pusher member 96 or another suitable deployment device. The pusher member 96 and the fastener 94 can be advanced over the suture 80 through the lumen 26 (after removing the needle 20) or through another lumen in the shaft 24. In one implementation, the fastener 94 be a suture clip, which can be configured to slide along the suture 80 in one direction and resist movement along the suture in the opposite direction, thereby maintaining tension on the suture and resisting pull-through of the suture once the clip is positioned at its desired location. In another implementation, the fastener 94 can comprise a crimpable fastener that can be slid along the suture to its desired location and then crimped in place on the suture. Various suture clips, other types of suture fasteners, and deployment techniques for suture fasteners that can be used in the methods disclosed in the present application are disclosed in U.S. Publication Nos. 2014/0031864 and 2008/0281356 and U.S. Pat. No. 7,628,797, which are incorporated herein by reference.

As shown in FIG. 22, after deployment of the fastener 94, the pusher member 96 and the shaft 24 can be removed from the patient's body and the suture can be severed proximal to the fastener 94. In alternative embodiments, in lieu of or in addition to the use of suture 80, the folds of tissue 74 can be secured to each other using other techniques and mechanisms, such as by applying a biocompatible adhesive between the folds of the tissue, as described in U.S. Publication No. 2016/0287383. The adhesive can be dispensed, for example, from apertures in the leaflet-capture arms 32, 34. In another implementation, in lieu of or in addition to the use of suture 80, one or more fasteners, such as a staple or a leaflet clip, can be implanted on the tissue 74. One example of such a clip is disclosed in U.S. Pat. No. 7,011,669, which is incorporated herein by reference.

It should be noted that the positioning of the disclosed devices can be confirmed visually using imaging modalities such as fluoroscopy, X-ray, CT, and MR imaging. Echocardiography in either 2D or 3D can also be used to help guide positioning the various components of the repair apparatus.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present, or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the native leaflet on which a procedure is being performed. As used herein, the term "distal" refers to a position, direction, or portion of a device that is further away from the user and closer to the leaflet. Thus, for example, proximal motion of a device is motion of the device away from the leaflet and toward the user (e.g., out of the patient's body), while distal motion of the device is motion of the device away from the user and toward the leaflet (e.g., into the patient's body). The terms "longitudinal" and "axial" refer to an axis extending in the proximal and distal directions, unless otherwise expressly defined.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

The invention claimed is:

1. An apparatus for repairing a leaflet of a valve of a heart, the valve having an annulus, and the apparatus comprising a leaflet-plicating tool that comprises:
   leaflet-capture arms, each comprising an arm-shaft and a leaflet-engaging member disposed in the arm-shaft; and
   a helical needle operatively coupled to the leaflet-capture arms, the helical needle comprising a needle-shaft that defines a needle axis of the helical needle, and a helical portion that extends helically around the needle axis distally away from the needle-shaft,
   the leaflet-plicating tool configured to:
   use the leaflet-capture arms, extended over the leaflet from the annulus toward a free edge of the leaflet, to form a plication in the leaflet of the valve between the leaflet-capture arms; and
   subsequently secure the plication by using the helical needle to stitch a suture helically along the plication.

2. The apparatus according to claim 1, wherein the leaflet-plicating tool is configured to form the plication by pivoting the leaflet-capture arms toward each other.

3. The apparatus according to claim 1, wherein the helical portion is more flexible than the needle-shaft.

4. The apparatus according to claim 1, wherein the helical portion has a plurality of coils extending helically along the needle axis.

5. The apparatus according to claim 4, wherein a diameter of the coils of the plurality of coils is uniform.

6. The apparatus according to claim 4, wherein a diameter of the plurality of coils increases distally along the needle axis.

7. The apparatus according to claim 4, wherein:
   the helical portion has (i) a proximal region that includes a proximal end at which the helical portion is coupled to the needle-shaft, (ii) a distal region that includes a distal tip of the needle, and (iii) an intermediate region between the proximal region and the distal region, and
   the intermediate region is wider than the proximal region and wider than the distal region.

8. The apparatus according to claim 1, wherein the leaflet-plicating tool:
   comprises a tool-shaft having a longitudinal axis and comprising an inner lumen and an outer lumen, the inner lumen comprising internal threads along a distal portion thereof, and is configured to advance the helical needle through the inner lumen by rotating the helical needle while coils of the helical needle are threadedly engaged with the internal threads.

9. The apparatus according to claim 8, wherein the outer lumen is C-shaped.

10. The apparatus according to claim 9, wherein:
the leaflet-capture arms are disposed through the C-shaped outer lumen, and
the leaflet-plicating tool is configured to form the plication between the leaflet-capture arms by sliding the leaflet-capture arms, within the C-shaped outer lumen, along a curved path toward each other.

11. The apparatus according to claim 1, wherein the arm-shaft of each leaflet-capture arm has a C-shaped cross-sectional profile; and defines an arm-shaft lumen having a substantially circular cross-section; and extending along the leaflet-capture arm, eccentrically with respect to the C-shaped cross-sectional profile of the arm-shaft.

12. The apparatus according to claim 11, wherein each leaflet-engaging member:
is slidable and rotatable within the arm-shaft lumen, and
has a distal end portion that is configured to:
be retained in a substantially linear state within the arm-shaft lumen of the respective arm-shaft, and
deflect to form a hook responsively to being deployed from the arm-shaft lumen.

13. The apparatus according to claim 12, wherein the leaflet-plicating tool is configured to:
position the hook around the free edge of the leaflet, and
form the plication at least in part using the leaflet-capture arms while (i) the leaflet-capture arms are extended over the leaflet from the annulus toward the free edge of the leaflet, and (ii) each hook remains positioned around the free edge of the leaflet.

14. The apparatus according to claim 13, wherein the leaflet-plicating tool is configured to form the plication at least in part by rotating the leaflet-engaging members while each hook remains positioned around the free edge of the leaflet between the leaflet-capture arms.

15. The apparatus according to claim 13, wherein the leaflet-plicating tool is configured to, for each of the leaflet-capture arms, position the hook around the free edge of the leaflet by sliding the leaflet-engaging member proximally through the arm-shaft lumen.

16. The apparatus according to claim 1, wherein the leaflet-capture arms are biased to an open position by a biasing member, the biasing member comprising a spring selected from the group consisting of: a U-shaped spring, a coil spring, and a torsion spring.

17. The apparatus according to claim 1, wherein the leaflet-capture arms are biased to an open position by a biasing member, the biasing member comprising an elastomeric component positioned between the leaflet-capture arms.

18. The apparatus according to claim 1, wherein the leaflet-capture arms comprise a first leaflet-capture arm and a second leaflet-capture arm, and wherein the apparatus further comprises an actuator:
extending out of an opening in the arm-shaft of the first leaflet-capture arm, to the second leaflet-capture arm, and
extending, from the opening, proximally through the arm-shaft of the first leaflet-capture arm, such that proximally sliding the actuator through the arm-shaft of the first leaflet-capture arm pulls the second leaflet-capture arm toward the first leaflet-capture arm.

19. The apparatus according to claim 18, wherein the actuator is a first actuator, and wherein the apparatus further comprises a second actuator:
extending out of an opening in the arm-shaft of the second leaflet-capture arm, to the first leaflet-capture arm, and
extending, from the opening in the arm-shaft of the second leaflet-capture arm, proximally through the arm-shaft of the second leaflet-capture arm, such that proximally sliding the second actuator through the arm-shaft of the second leaflet-capture arm pulls the first leaflet-capture arm toward the second leaflet-capture arm.

20. A method for plicating a leaflet of a valve of a heart of a patient, using a leaflet-plicating tool, the method comprising:
inserting into the heart the leaflet-plicating tool including first and second leaflet-engaging members disposed within first and second leaflet-capture arms disposed within a tool-shaft;
extending the first and second leaflet-engaging members out of the first and second leaflet-capture arms, respectively;
positioning the leaflet-capture arms such that each leaflet-engaging member extends over a leaflet from an annulus of the valve toward a free edge of the leaflet,
subsequently forming a plication in the leaflet of the valve between the leaflet-engaging members, and
securing the plication by using a helical needle, deployed from within a needle-shaft of the leaflet-plicating tool, to stitch a suture helically along the plication.

21. The method according to claim 20, wherein the valve is a tricuspid valve, and the plication is performed on the leaflet of the tricuspid valve.

22. The method according to claim 20, wherein forming the plication comprises forming the plication in the leaflet of the valve by pivoting the leaflet-capture arms toward each other while retracting the leaflet-engaging members proximally as the leaflet-engaging members remain extended over the free edge of the leaflet.

23. The method according to claim 20, wherein:
the leaflet-engaging member has a distal end portion configured to form a hook when deployed from the arm-shaft to extend around the free edge of the leaflet, and
positioning the leaflet-capture arms such that each leaflet-engaging member extends over the leaflet comprises positioning the leaflet-capture arms such that the hook extends around the free edge of the leaflet.

24. The method according to claim 20, wherein the tool-shaft includes a C-shaped lumen, and wherein positioning the leaflet-capture arms comprises extending the first and second leaflet-capture arms through the C-shaped lumen in a manner that the leaflet-capture arms diverge outward along separate curved paths over the leaflet from the annulus toward the free edge of the leaflet.

25. An apparatus for repairing a leaflet of a valve of a heart, the valve having an annulus, and the apparatus comprising a leaflet-plicating tool that comprises:
a first leaflet-capture arm and a second leaflet-capture arm, each leaflet-capture arm comprising an arm-shaft and a leaflet-engaging member disposed in the arm-shaft;
an actuator extending:
out of an opening in the arm-shaft of the first leaflet-capture arm, to the second leaflet-capture arm, and
from the opening, proximally through the arm-shaft of the first leaflet-capture arm, such that proximally sliding the actuator through the arm-shaft of the first leaflet-capture arm pulls the second leaflet-capture arm toward the first leaflet-capture arm; and a helical needle, operatively coupled to the first leaflet-capture arm and the second leaflet-capture arm, configured to:

use the first leaflet-capture arm and the second leaflet-capture arm, extended over the leaflet from the annulus toward a free edge of the leaflet, to form a plication in the leaflet of the valve between the leaflet-capture arms; and subsequently secure the plication by using the helical needle to stitch a suture helically along the plication.

26. The apparatus according to claim 25, wherein:

the actuator is a first actuator;

the opening is a first opening; and the apparatus further comprises:

a second opening in the arm-shaft of the second leaflet-capture arm; and a second actuator:

extending out of an opening, to the first leaflet-capture arm, and extending, from the opening in the arm-shaft of the second leaflet-capture arm, proximally through the arm-shaft of the second leaflet-capture arm, such that proximally sliding the second actuator through the arm-shaft of the second leaflet-capture arm pulls the first leaflet-capture arm toward the second leaflet-capture arm.

\* \* \* \* \*